(12) United States Patent
Hodroff et al.

(10) Patent No.: US 7,740,576 B2
(45) Date of Patent: Jun. 22, 2010

(54) ARTICLES, DEVICES, AND METHODS FOR PELVIC SURGERY

(75) Inventors: Marc A. Hodroff, Portland, ME (US); James E. Cox, Corcoran, MN (US); Kimberly A. Anderson, Eagan, MN (US); Mark S. Bouchier, Lakeville, MN (US)

(73) Assignee: AMS Research Corporation, Minnetonka, MN (US)

( * ) Notice: Subject to any disclaimer, the term of this patent is extended or adjusted under 35 U.S.C. 154(b) by 999 days.

(21) Appl. No.: 11/398,368

(22) Filed: Apr. 5, 2006

(65) Prior Publication Data

US 2006/0260618 A1 Nov. 23, 2006

Related U.S. Application Data

(60) Provisional application No. 60/668,287, filed on Apr. 5, 2005, provisional application No. 60/668,397, filed on Apr. 5, 2005.

(51) Int. Cl.
*A61F 2/00* (2006.01)
*A61F 2/02* (2006.01)
(52) U.S. Cl. .......................................... 600/29; 600/30
(58) Field of Classification Search ............. 600/29–30, 600/37; 128/898
See application file for complete search history.

(56) References Cited

U.S. PATENT DOCUMENTS

| | | | |
|---|---|---|---|
| 5,840,011 A | 11/1998 | Landgrebe et al. | |
| 6,652,450 B2 * | 11/2003 | Neisz et al. | 600/30 |
| 7,070,556 B2 | 7/2006 | Anderson et al. | |
| 7,500,945 B2 * | 3/2009 | Cox et al. | 600/37 |
| 2002/0028980 A1 * | 3/2002 | Thierfelder et al. | 600/37 |
| 2002/0055748 A1 * | 5/2002 | Gellman et al. | 606/139 |
| 2002/0099258 A1 * | 7/2002 | Staskin et al. | 600/29 |
| 2002/0103542 A1 | 8/2002 | Bilbo | |
| 2003/0171644 A1 | 9/2003 | Anderson et al. | |
| 2003/0176762 A1 | 9/2003 | Kammerer | |
| 2003/0220538 A1 * | 11/2003 | Jacquetin | 600/37 |
| 2004/0087970 A1 * | 5/2004 | Chu et al. | 606/119 |

(Continued)

FOREIGN PATENT DOCUMENTS

EP 1 320 336 B1 7/2005

(Continued)

OTHER PUBLICATIONS

Papa Petros, "Vault Prolapse II: Restoration of Dynamic Vaginal Supports by Infracoccygeal Sacropexy, an Axial Day-Case Vaginal Procedure," International Urogynecology Journal, 12:296-303, 2001.

(Continued)

*Primary Examiner*—Charles A Marmor, II
*Assistant Examiner*—Catherine E Burk
(74) *Attorney, Agent, or Firm*—Jose' W. Jimenez; Kimberly K. Baxter; Gregory L. Koeller

(57) ABSTRACT

Described are implants, tools, and related methods, for use in pelvic surgery to treat conditions such as prolapse and incontinence, including one embodiment of a method that uses a transcoccyx tissue path; other embodiments that use particular implants with various features relating to, e.g., end portions; and other embodiments relating to particular tools.

15 Claims, 17 Drawing Sheets

U.S. PATENT DOCUMENTS

| | | |
|---|---|---|
| 2004/0249473 A1* | 12/2004 | Delorme et al. .......... 623/23.64 |
| 2004/0267088 A1 | 12/2004 | Kammerer |
| 2005/0008708 A1 | 1/2005 | Dai et al. |
| 2005/0131393 A1 | 6/2005 | Chu et al. |
| 2005/0245787 A1 | 11/2005 | Cox et al. |
| 2006/0058575 A1 | 3/2006 | Zaddem et al. |
| 2006/0122457 A1 | 6/2006 | Kovac et al. |

FOREIGN PATENT DOCUMENTS

| | | |
|---|---|---|
| WO | WO 02/22184 A2 | 3/2002 |
| WO | WO 02/091950 A1 | 11/2002 |
| WO | WO 03/028585 A2 | 4/2003 |
| WO | WO 03/045226 A2 | 6/2003 |
| WO | WO 03/047476 A1 | 6/2003 |
| WO | WO 03/068107 A1 | 8/2003 |
| WO | WO 03/073960 A1 | 9/2003 |
| WO | WO 03086205 A2 * | 10/2003 |
| WO | WO 03/096929 A1 | 11/2003 |
| WO | WO 2004/012626 A1 | 2/2004 |
| WO | WO 2004/041115 A2 | 5/2004 |
| WO | WO 2004/045457 A1 | 6/2004 |
| WO | WO 2005/004727 A1 | 1/2005 |
| WO | WO 2005/046511 A2 | 5/2005 |
| WO | WO 2005/087153 A2 | 9/2005 |
| WO | WO 2005/094741 A1 | 10/2005 |
| WO | WO 2005/112842 A1 | 12/2005 |
| WO | WO 2006/007189 A1 | 1/2006 |
| WO | WO 2006/007190 A1 | 1/2006 |
| WO | WO 2006/015031 A2 | 2/2006 |
| WO | WO 2006/031879 A1 | 3/2006 |

OTHER PUBLICATIONS

Farnsworth, B.N., "Posterior Intravaginal Slingplasty (Infracoccygeal Sacropexy) for Sever Posthysterectomy Vaginal Vault Prolapse—A Preliminary Report on Efficacy and Safety," International Urogynecology Journal, 13:4-8, 2002.

Kettel, L.M. et al., "An Anatomic Evaluation of the Sacrospinous Ligament Colpopexy," Surg. Gynecol. Obstet., 168(4):318-22, Apr. 1989.

Buller, J.L. et al., "Uterosacral Ligament: Description of Anatomic Relationships to Optimize Surgical Safety," Obstet. Gynecol. 97:873-879, 2001.

Flynn, B.J. et al., "Surgical management of the apical vaginal defect," Curr. Opin. Urol. 12(4):353-358, Jul. 2002.

Brochure, "GPS for Pelvic Floor Repair," Gynecare Prolift, 6 pages, 2005.

* cited by examiner

ARTICLES, DEVICES, AND METHODS FOR PELVIC SURGERY

PRIORITY CLAIM

The present non-provisional patent Application claims priority under 35 USC §119(e) from U.S. Provisional Patent Applications having Ser. No. 60/668,287, filed on Apr. 5, 2005, by Hodroff and titled VAGINAL VAULT PROLAPSE, and 60/668,397, filed on Apr. 5, 2005, by Cox et al. and titled ARTICLES, DEVICES AND METHODS FOR PELVIC SURGERY, wherein the entirety of said provisional patent applications are incorporated herein by reference.

FIELD OF THE INVENTION

Described herein are features of surgical articles, surgical methods, and surgical tools, for use in the field of urogenital surgery, e.g., to install support devices for use in treating vaginal vault prolapse, incontinence, etc.

BACKGROUND

Medical conditions of urinary incontinence and pelvic prolapse are conditions of great importance. An aging population can be prone to such conditions.

Urinary incontinence and pelvic prolapse are related to tissues of the pelvic region such as the bladder, urethra, and the vaginal vault. Pelvic prolapse develops when intra-abdominal pressure, muscle failure, a surgical procedure such as a hysterectomy, or other factors, allow or cause a pelvic organ such as the vagina to become displaced. Within the general category of pelvic organ prolapse, specific types include vault prolapse (apical) such as enterocele; cystocele (anterior); rectocele (posterior); and combinations of these.

Various techniques have been designed to correct or ameliorate vaginal vault prolapse and its symptoms, with varying degrees of success. Nonsurgical treatments involve measures to improve the factors associated with prolapse, including treating chronic cough, obesity, and constipation. Other nonsurgical treatments may include pelvic muscle exercises or supplementation with estrogen.

A variety of surgical procedures have also been attempted for the treatment of pelvic conditions such as vaginal vault prolapse and urinary incontinence. See for example U.S. patent application Ser. No. 10/834,943, entitled "Method and Apparatus for Treating Pelvic Organ Prolapse," filed Apr. 30, 2004, and Ser. No. 10/306,179, entitled "Transobturator Surgical Articles and Methods," filed Nov. 27, 2002, the entireties of each of these two patent applications being incorporated herein by reference. Such patent applications describe articles and methods for treating incontinence and pelvic organ prolapse by use of a support member for supporting specific tissue. U.S. application Ser. No. 10/834,943, for example, discusses a support member that includes a central tissue support portion and two end portions, and related methods for implantation. The central tissue support portion can be attached at tissue of a prolapsed organ, e.g., at the posterior of the vaginal vault. The end portions of the support member are then positioned through respective tissue pathways to place the support member in a therapeutic position for treatment of the prolapsed organ.

SUMMARY

The invention includes various features of pelvic surgical procedures, implants, and tools for surgical implantation procedures.

In one respect the invention relates to surgical methods that place an end portion of an implant through a region near the coccyx bone, i.e., a "coccyx" or "transcoccyx" tissue path. The invention also relates to devices, including tools and implants, that may be useful for treatments according to this "transcoccyx method," but that may also be useful for other treatments, and for other installation methods.

For example, described are tools for surgically implanting an implant. The tools may be useful for treatments according to the "transcoccyx method," but may also be useful for other treatments and for other installation methods. Likewise, the tools may be useful for installing implants as described herein, but they may also be useful for installing other implants.

The invention includes any one or more of the above discussed implants, tools, or methods, any of which can be used separately, or in any possible combination, as will be understood based on the following description.

According to certain embodiments an implant can be used to treat vaginal vault prolapse. The support member can include a central portion that can be attached to tissue of the vaginal vault, and two end portions attached to the central portion. The implant can be used to place vaginal vault tissue in a therapeutic position for treatment of vaginal vault prolapse by attaching the central portion of the support member to tissue of the vaginal vault and attaching the end portions to separate locations for positioning or supporting the prolapsed tissue. Certain inventive methods involve placement of a support member to support prolapsed tissue, including placement of an end portion of the support member at a location proximal to the coccyx bone, e.g., through ischiococcygeous (i.e., "coccygeous") or iliococcygeous muscle lateral to the coccyx bone. Exemplary tissue paths can initiate from a region surrounding vaginal vault tissue and can extend past the rectum to a location proximal to the coccyx bone. The end portion of the support member can generally be guided through such a passage prepared in muscle or other tissue, past the rectum, past and proximal to the coccyx bone, and then through an external incision of the epidermis.

Embodiments of the inventive methods attach a tissue support portion of an implant to tissue of a vaginal vault, and one or two end portions, either unilaterally or bi-laterally, near the coccyx bone (e.g., proximal to the tip of the coccyx). Other placement of a tissue support portion, and other tissue paths, may be useful for use with inventive implants, methods, and tools described herein.

In one aspect, the invention relates to a method for supporting vaginal tissue. The method includes: providing an implant comprising a tissue support portion and an end portion extending from the tissue support portion; creating a vaginal incision; placing the tissue support portion in contact with vaginal tissue in a position to support the vaginal tissue; and producing a tissue path between the position of the tissue support portion and an exterior incision. The tissue path passes through tissue of a coccyx region bounded by an upper edge of a sacrospinous ligament, a tip of a coccyx bone, a point approximately 2.5 centimeters lateral to the tip of the coccyx bone, and an ischial spine. The end portion is extended through the tissue path to the external incision. The implant may be any implant as described herein or otherwise, and may or may not include features of implants and end portions as described herein, such as a dilator, sheath, etc. The method may include the use of a tool, the tool being as specifically described herein or otherwise.

In another aspect, the invention relates to a pelvic implant. The implant may be useful for supporting pelvic tissue and can include supportive portions consisting of: a central support portion having two elongate end portions extending from the central support portion. The central support portion has a width greater than a width of the end portions. The implant also includes a shorter end portion that has a length that is shorter than a length of a longer end portion. The implant may optionally include one or more sheath, each at least partially containing an end portion, and a dilator for each end portion. The implant may be implanted into a patient by any method such as a transcoccyx method described herein, or otherwise. The implant may be used to treatment any pelvic condition.

Another aspect of the invention relates to a pelvic implant that includes: a tissue support portion and an elongate end portion extending from the tissue support portion, a dilator attached to a distal end of the end portion, and an elongate sheath surrounding at least a portion of the end portion. A distal end of the sheath is also attached to the dilator, and the end portion includes a passage between a location inside of the sheath to an internal surface of the dilator. The implant may be implanted into a patient by any method such as a transcoccyx method described herein, or otherwise. The implant may be used to treatment any pelvic condition.

In another aspect, the invention relates to a method of connecting a dilator to an end portion of an implant. The method includes: providing an elongate end portion having a distal end, providing an elongate sheath surrounding at least a distal portion of the end portion, laterally curling a distal portion of the sheath and end portion, and molding a dilator over the curled sheath and end portion. The method results in a molded dilator assembly that includes the dilator molded to distal ends of each of the sheath and end portion. The molded dilator assembly includes a passage that allows access from an interior location of the sheath to an internal surface of the dilator. A needle can pass through the passage to allow the tip of the needle to engage an internal surface of the dilator. The implant may be implanted into a patient by any method such as a transcoccyx method described herein, or otherwise, and with any type of needle. The implant may be used to treatment any pelvic condition.

In yet another aspect, the invention relates to a surgical tool that includes a handle comprising a longitudinal axis and a two-dimensional elongate needle extending from the handle. The elongate needle includes: a first curved portion extending longitudinally from the handle, the first curved portion having a first radius of curvature and a first arclength; a second curved portion extending from a distal end of the first curved portion, the second curved portion having a second radius of curvature and a second arclength that are different from (e.g., less than) the first radius of curvature and first arclength; and a straight portion extending from a distal end of the second curved portion to a needle tip. The tool may be useful for transvaginal "inside-out" procedures for implanting a pelvic implant, e.g., using a transcoccyx tissue path as described herein, or using a different tissue path.

In yet another aspect, the invention relates to a pelvic implant for supporting vaginal tissue. The implant includes: a tissue support portion having an anterior portion, a posterior portion, and a mid-portion between the anterior portion and the posterior portion; at least two end portions extending from one or more of the mid-portion or the anterior portion, and only one end portion extending from the posterior portion. The implant and end portions may optionally include features of sheaths, dilators, etc., as described herein.

In another aspect, the invention relates to an implant comprising supportive portions consisting of: a tissue support portion, and one end portion extending from the tissue support portion. The implant and end portion may optionally include features of sheaths, dilators, etc., as described herein.

Figure 1:
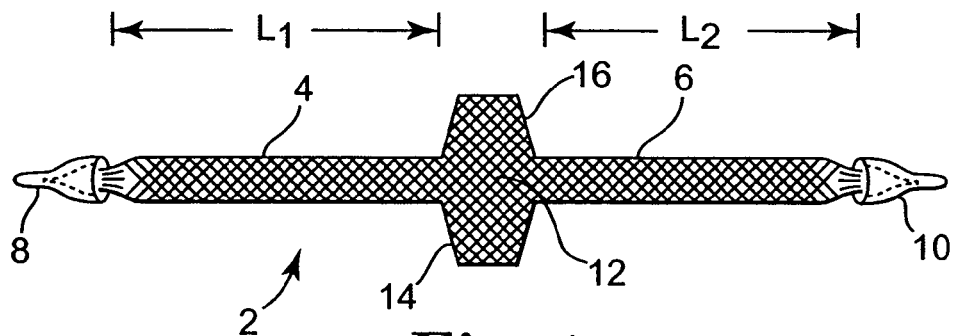
FIG. 1 illustrates an example of an implant according to the invention.

All drawings are schematic and not to scale.

DETAILED DESCRIPTION

According the invention, a surgical implant is used to treat a medical condition, including the specific examples of implanting a support member ("implant") to treat a pelvic condition such as vaginal vault prolapse or incontinence (male or female). Described herein are various features of surgical implants, surgical tools, and surgical methods, useful for installing implants.

An implant can be implanted to treat disorders such as urge incontinence, mixed incontinence, overflow incontinence, functional incontinence, prolapse (e.g. vaginal), enteroceles (e.g. of the uterus), rectoceles, cystocele, and anatomic hypermobility.

In general, an implant can include a tissue support portion that can be used to support a pelvic tissue such as the urethra or vaginal tissue. During use, the tissue support portion is typically placed in contact with and attached to tissue to be supported, such as with a suture. An implant can additionally include one or more end portions attached to the tissue support portion. See, e.g.: U.S. patent application Ser. Nos. 10/834,943; 10/306,179; U.S. Ser. No. 11/347,063, filed Feb. 3, 2006, entitled PELVIC IMPLANTS AND RELATED METHODS; U.S. Ser. No. 11/347,596, filed Feb. 3, 2006, entitled SURGICAL IMPLANTS AND RELATED METHODS AND SYSTEMS; and U.S. Ser. No. 11/346,750, filed Feb. 3, 2006, entitled TRANSOBTURATOR SURGICAL ARTICLES AND METHODS; the entireties of each of these being incorporated herein by reference.

An implant may include sections that are synthetic or of biological material (e.g., porcine, cadaveric, etc.). End portions may be, e.g., a synthetic mesh such as polypropylene. The tissue support portion may be synthetic (e.g., a polypropylene mesh) or biologic. Examples of support member products that are sold commercially include a number sold by American Medical Systems, Inc., of Minnetonka Minn., under the trade names Apogee® and Perigee® for use in treating pelvic prolapse (including vaginal vault prolapse, cystocele, enterocele, etc.), and Sparc®, Bioarc®, and Monarc® for treating urinary incontinence.

Exemplary implants can include a tissue support portion for placing in contact with tissue to be supported, and one or more "extension" portions (or "end portions"), the tissue support portion being useful to support a specific type of pelvic tissue such as the urethra, bladder, or vaginal tissue (anterior, posterior, apical, etc.). The tissue support portion can be sized and shaped to contact the desired tissue when installed, e.g., as a sling, to contact and support tissue. A tissue support portion that is located between two or more extension or end portions is sometimes referred to herein as a "central support portion."

End portions are elongate pieces of material that extend from the tissue support portion and are connected to the tissue support portion, useful to attach to other anatomical features and thereby provide further support for the tissue support portion and the supported tissue. One or multiple (e.g., one, two, or four) end portions can extend from the tissue support portion as elongate "ends," "arms," or "extensions," that are used to attach to other anatomy, such as by extending through a tissue path to an external incision or to an internal anchoring point.

Dimensions of an implant can be as desired and useful for any particular installation procedure or treatment, and to support a specific tissue or type of tissue. Exemplary dimensions can be sufficient to allow the tissue support portion to contact tissue to be supported, and to allow one or more end portion to extend from the tissue support portion to a desired anatomical location to allow the end portion be anchored to support the tissue support portion.

A tissue support portion for contacting and supporting tissue can optionally and normally be of a width that is greater than a width of an end portion. For an implant that includes either a single end portion or only two end portions, an increased width of a tissue support portion may take the form of one or two lateral extensions that extend the width of the central support portion in at least one direction, beyond the width of an end portion. Optionally a tissue support portion may include two lateral extensions in each of an anterior lateral direction and a posterior lateral direction, e.g., relative to the width of an end portion or portions. A portion of a tissue support portion that is between an anterior extension and a posterior extension can be considered a mid-portion.

A tissue support portion should be sized and shaped to an overall area for contacting tissue being supported. The tissue support portion is of sufficient length to at least partially surround or otherwise be in contact with pelvic tissue to be supported. Various shapes and sizes are useful, and the particular shape can depend on the intended application, e.g., to treat incontinence, vaginal prolapse, etc.

Generally, exemplary lengths of a tissue support portion can be in the range from 0.5 to 5 centimeters, such as from 0.7 to 4 centimeters. Exemplary widths of a tissue support portion can be in the range from 1 to 15 centimeters, such as from 2 to 12 centimeters. The shape of the tissue support portion can also be varied, depending on the intended application, and may be square, rounded, angled, rectangular, etc.

A width of an end portion can be a width useful for implanting the implant and for providing desired strength and fixation properties during and after implantation and optional tensioning of the sling. Typical widths of end portions can be in the range from 0.5 to 3 centimeters, e.g., from 0.8 to 2 centimeters. End portions can typically have a uniform or substantially uniform width along the length, normally not varying by more than about 25 percent of the average width along the length of the installed portion of the end portion.

An example of a particular type of pelvic implant is the type that includes supportive portions including or consisting of a central support portion and two elongate end portions extending from the central support portion. The term "supportive portions" refers to portions of an implant that function to support tissue after the implant has been implanted, and specifically includes end portions and tissue support portions, and does not include optional or appurtenant features of an implant such as a sheath or dilator.

According to particular embodiments, end portions may be of the same or of different lengths. End portions of different lengths may be useful for certain types of surgical implantation procedures where one end portion is inserted internally into a patient during an earlier step, and a second end portion is inserted in a later step, optionally using the same tool for both steps. As an example, a procedure described herein for treating a female pelvic condition using a transvaginal "transcoccyx" tissue path (e.g., an "inside-out" transcoccyx implantation method as described herein), may benefit from the use of an implant that includes two end portions of different lengths. One end portion may be shorter, for first insertion into a patient and adjustment into position, and a second end portion may be longer for insertion after the shorter end portion. The longer end portion, inserted second, includes an extended length that allows the surgeon to manipulate the second portion while the first portion is already inserted and therefore is immobile.

The lengths of end portions can be measured as from a location where an end portion meets a tissue support portion, to an opposite distal end of an end portion such as where the end portion meets a dilator. Exemplary lengths of a longer end portion may be from 1 to 4 inches longer than a shorter end portion, e.g., from 1 to 3 inches longer. Examples of specific end portion lengths may be, e.g., from 7 to 11 inches for a shorter end portion and from 8 to 12 inches for a longer end portion (e.g., from 9 to 11 inches).

FIG. 1 illustrates an example of an implant, 2, that has supportive portions consisting of a central support portion 12 and two end portions 4 and 6. Central support portion 12 includes anterior lobe 16 and posterior lobe 14 (with a mid-portion between the two lobes). End portions 4 and 6 connect to central support portion 12 and extend in opposite directions to distal ends that include dilators 8 and 10, which both point in directions that are parallel to the length-wise axis of end portions 8 and 10. As shown (not necessarily to scale), end portion 4 has a length that is less than the length of end portion 6, e.g., by a difference in the range from 1 to 4 inches.

Figure 2:
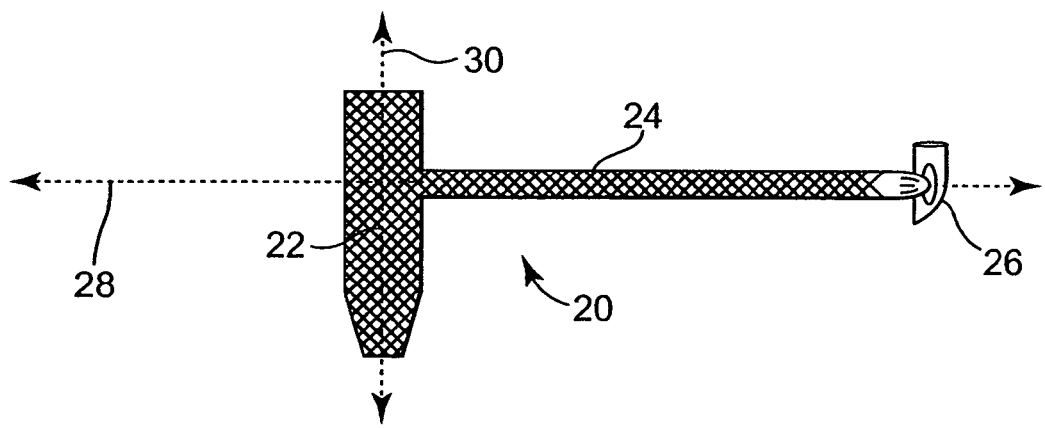
FIG. 2 illustrates an example of an implant according to the invention.
Figure 3:
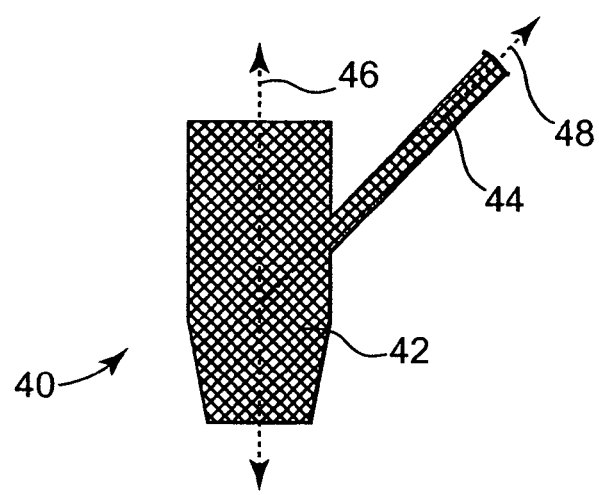
FIG. 3 illustrates an example of an implant according to the invention.

In another aspect, the invention can relate to the design and use of a support member (implant) that includes only one end portion, e.g., the implant being useful for treating vaginal vault prolapse. Such as single-sided or "one-legged" implant is illustrated in FIGS. 2 and 3, which illustrate an implant that may be useful for vault support and that has only one support arm (end portion) attached to a tissue support portion. Referring to FIG. 2, implant 20 includes supportive portions that consist of tissue support portion 22 and end portion 24. End portion 24 is attached to give a 90 degree angle between length-wise axis 28 of end portion 24 and lateral axis 30 of tissue support portion 22, but may alternately create a non-perpendicular angle.

A different example of a feature of a useful implant can be an end portion extended from a tissue support portion at an angle that is not perpendicular to a lateral axis of the tissue support portion. A non-perpendicular angle between a lateral axis of the tissue support portion and a length-wise axis of an attached end portion can allow the tissue support portion to be in contact with tissue, while the end portion extends through or to desired anatomy, without causing a fold or bend in material at the end portion or at the transition between an end portion and a tissue support portion. The angle (measured while the implant lies flat) may be as desired for a particular procedure, but an angle of approximately 45 degrees may be useful for treatment of vaginal prolapse by placement of the tissue support portion at the vaginal apex and extension of an end portion through a tissue path that includes a coccyx region location as described herein. The angle may be, for example, between 40 and 50 degrees, e.g., from 35 to 55 degrees, or from 30 to 60 degrees, as measured from between a line defined by the lateral axis of the tissue support portion and a length-wise axis of the end portion, while the implant lies flat.

Figure 4:
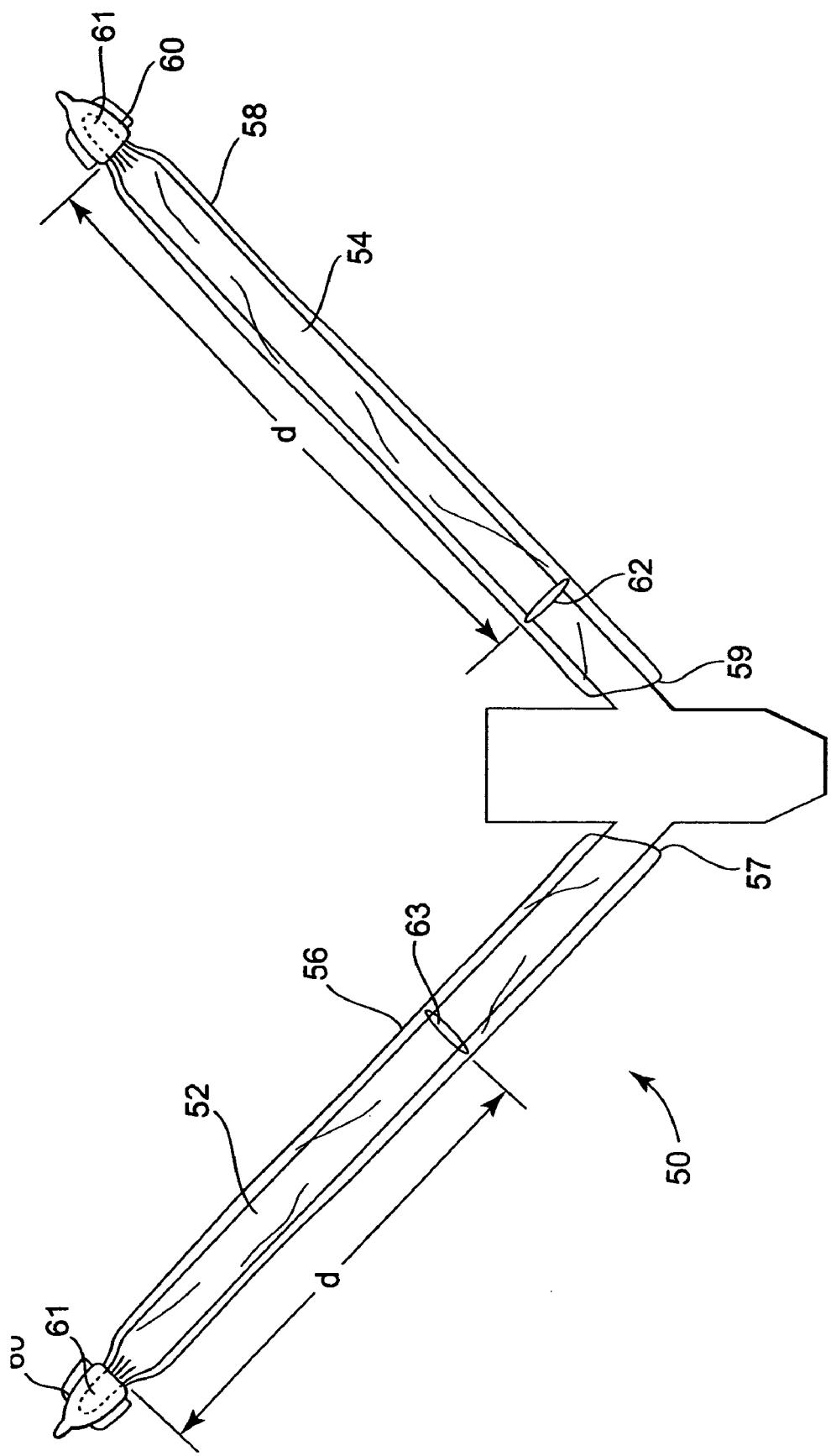
FIG. 4 illustrates an example of an implant according to the invention.

FIG. 3 illustrates an embodiment of an implant having an end portion at a non-perpendicular angle to a tissue support portion as described. Implant 40 includes supportive portions that consist of tissue support portion 42 and end portion 44. End portion 44 is attached to give a 45-degree angle between length-wise axis 48 of end portion 44 and lateral axis 46 of tissue support portion 42. While FIG. 3 shows an implant that includes only one end portion, the same feature of an end portion angled relative to a tissue support portion could be used also with an implant that includes supportive portions consisting of a central support portion and two end portions, such as illustrated at FIG. 4.

According to other embodiments of implants, various additional components and features can be incorporated for added utility or convenience, such as components and features that facilitate surgical implantation. For instance, a tensioning member (e.g., suture) may be attached to an implant along a portion or entire length of an end portion for use in adding tension or in positioning an implant or a portion (e.g., end portion) of an implant. A tensioning suture may be attached at one or multiple attachment points along a length of an end portion. Multiple sutures may be used, such as two or more sutures along a length of one end portion, for added tensioning effect. Alternately or in addition, end portions of an implant can include reinforcement or multiple layers. See, e.g., Assignee's copending U.S. patent application Ser. No. 11/347,063, and U.S. Ser. No. 11/347,596. Other embodiments of the invention do not require and can specifically exclude a tensioning member such as a suture, multiple layers for end portions, and edge extension reinforcement for end portions.

Yet another optional component of an implant can be a sheath such as a plastic, transparent elongate tube, or the like, that can cover a portion or entire length of an end portion of an implant to facilitate installation by allowing a surgeon to apply tension or pressure on the sheath, optionally to indirectly pressure or tension the end portion or tissue support portion.

An end portion of an implant may also optionally include a connector or "dilator" at an end distal from a tissue support portion, the dilator being able to cooperate with an insertion tool (e.g., needle, tunneler, etc.) during a surgical procedure to either push or pull the connector through tissue using the end of the insertion tool. For example, a connector may be a rigid plastic tip or dilator attached to a distal end of an end portion of an implant, and constructed to attach to an end of an elongate insertion tool by snapping, threading, or otherwise securing to the end of the insertion tool. The insertion tool can then be used to push or pull the connector through a tissue passage to also bring the end portion of the implant through the tissue passage.

A dilator can be oriented as desired relative to an end portion, and may optionally be oriented to point in a direction that is approximately parallel to a length-wise axis of an end portion (when the end portion of the implant lies flat) as illustrated, e.g., at FIGS. 1 and 4. For example, exemplary dilators may include a major dimension that will align the dilator along a tissue path as the dilator dissects the tissue path or traverses a pre-formed tissue path. The major dimension may also align with an insertion tool to which the dilator is attached. According to certain end portions and dilator embodiments, the major dimension of a dilator can still further be aligned with a length-wise axis of an end portion, e.g., in a manner to allow the dilator to be pushed through tissue by use of a needle that engages the needle from behind the dilator and pushes the dilator through the tissue path.

FIG. 4 shows implant 50 that includes end portions 52 and 54, each of which is enclosed in a plastic sheath 56 and 58, respectively. Each sheath 56 and 58 includes end opening 57 and 59, respectively. As illustrated, plastic sheath 56 and end portion 52 are longer in length compared to end portion 54 and sheath 58. Sheaths 56 and 58 include apertures 63 and 62, respectively, located on a side of each sheath to allow a needle to be inserted into the sheath. Distance (d) between each aperture 63 and 62 and each dilator 60, is equal (e.g., within 5 percent), even though sheath 56 is longer than sheath 58. The equal length (d) allows a single needle of one length to be inserted into each end portion so that a tip of the needle engages a dilator 60, while the same amount (length) of needle is located inside each of the two different sheaths.

Figure 5:
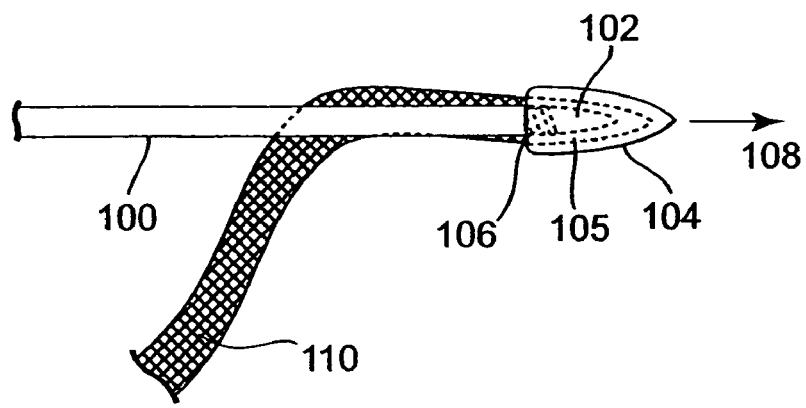
FIG. 5 illustrates an example of a combination of an implant and a needle, according to the invention.

Still referring to FIG. 4, with regard to methods described herein, a needle (not shown) can be inserted into sheath 58 through aperture 62 and the tip of the needle can be led internally within the passage of sheath 58 to engage dilator 60 at the distal end of end portion 54, from within the sheath. The tip of the needle becomes located in internal space 61 (drawn as dashed lines) of dilator 60. This engagement between a dilator and needle tip is generally shown in FIG. 5. After the needle is used to surgically position end portion 54 as desired, the needle can be removed from sheath 62 and the same needle can be inserted into side aperture 63 of sheath 56 (both being located outside of the patient) and led internally through sheath 56 to engage dilator 60 at internal space 61.

This second end portion and needle assembly can then be surgically implanted in the patient. Distance (d) for each of sheaths 56 and 58 having different overall lengths is equal so that a single needle inserted into each sheath will extend through the same distance (d) of each sheath, to engage a dilator.

Alternately, only the longer sheath need have a side aperture for insertion of a needle. In such an embodiment, the total length of the shorter sheath between dilator and end opening can be equal to the distance between dilator and aperture for the longer sheath. A needle can be inserted into the end opening of the shorter sheath and the same needle can be inserted into the aperture of the longer sheath, and the same length of needle is still inserted into each sheath.

FIG. 5 illustrates a combination of a dilator and a needle wherein the needle engages the dilator in a manner that allows the needle to push the dilator to form a tissue path or to pass the dilator through a preformed tissue path. FIG. 5 shows needle 100, including threaded tip 102 engaged with dilator 104. Dilator 104 is also attached to a distal end of end portion 110 of an implant. Threads 106 are located on tip 102 of needle 100, to allow a frictional engagement with inside surface 105 of dilator 104; inside surface 105 of dilator 104 may not include opposing threads, but the size of the internal space may allow good frictional engagement between threads 106 and surface 105 of dilator 104. Threads 106 allow for a removable engagement between dilator 104 and tip 102.

As illustrated in FIG. 5, tip 102 engages dilator 104 in a direction that allows needle 100 to push dilator 104 in direction 108 (i.e., as a line extending from the end of needle 100), and to thereby pull end portion 110 through a tissue path. Afterward, still within a surgical implantation procedure, dilator 104 can be removed from threaded tip 102 and tool 100 can optionally be used to engage a second dilator at a second end portion of an implant, if desired, for placement of the second end portion within another tissue path. End portion 110 illustrated in FIG. 4 is not contained by a sheath, but a sheath could be used as discussed elsewhere in the present description, with needle 110 being inserted into the sheath to engage internal surface 105 of dilator 104.

Figure 6:
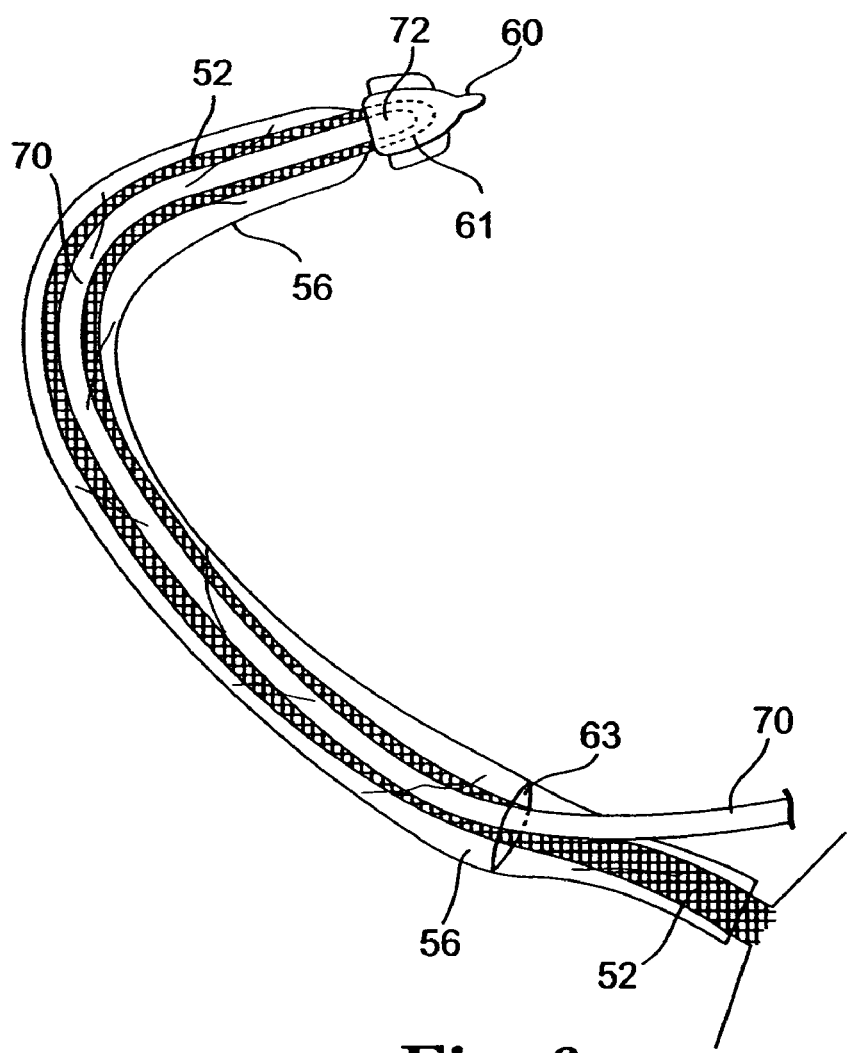
FIG. 6 illustrates an example of a combination of an implant and a needle, according to the invention.

FIG. 6 illustrates a needle and implant configuration wherein the needle is contained inside of a sheath. Needle 70, having tip 72, has been inserted into side aperture 63 of transparent plastic sheath 56, the sheath also containing end portion 52 of an implant. The arrangement places needle 70 and end portion 52 next to each other inside of sheath 56, for the length between side aperture 63 and dilator 60. The needle can be used to push dilator 60 and end portion 52 to form or traverse a tissue path, such as with dilator 60 becoming extended from an external incision and allowing dilator 60 to be removed from tip 72 and needle 70 to be removed from the inside of sheath 56. The same needle 70 can then, optionally, be used to place a second end portion of the implant (e.g., end portion 54 as shown in FIG. 5), into a second tissue path, if desired.

A distal end of an implant that includes a dilator, such as illustrated at FIGS. 1, 4, 5, and 6, advantageously are pushable through a tissue path using a needle engaged with the dilator at the side of the dilator that is attached to the distal end of an end portion. In addition, the dilator, sheath, and end portion assembly has a relatively low profile, meaning that it is somewhat streamlined and of a reduced or minimized cross section, which allows for ease of movement through a tissue path. The assembly can be prepared to exhibit a low profile based on the manner by which the distal ends of the sheath and end portion are assembled and connected to the dilator.

Figure 7:
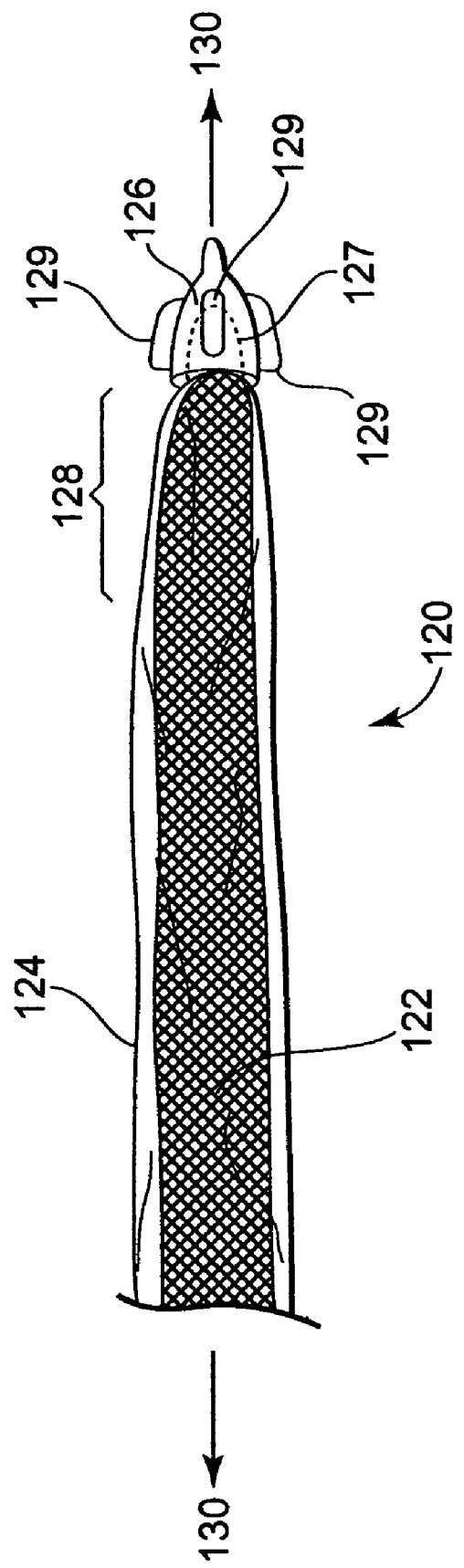
FIG. 7 illustrates an example of a distal portion of end portion of an implant of the invention.

FIG. 7 shows details of this streamlined or "low profile" end configuration. End 120 includes end portion 122 (a mesh) within sheath 124, and connected to dilator 126. As assembled, distal end region 128 includes a lateral curl or fold of the assembled end portion 122 and sheath 124, meaning the assembled pieces are together bent into an at least partial curve or coil around a co-extending lengthwise axis (130) of the sheath 122 and end portion 124. Axis 130 is also parallel to a major dimension (length) of dilator 126, and is also aligned with the direction in which the dilator can be pushed through a tissue path. A needle can be inserted into the interior of sheath 124, such as through a side aperture in the sheath, through an end opening in the sheath, or, if desired, by puncturing the sheath using the tip of the needle. Once the needle is inside of the sheath, a low profile end configuration allows the tip of the needle to pass along an internal length of the sheath and become engaged with the interior portion of the dilator from the direction of the sheath, such as by engaging an internal surface of hollow space 127 of dilator 126.

Another optional feature of a dilator is illustrated at FIG. 7, which is fins or extensions 129 of dilator 126. Extensions 129 extend in a direction away from lengthwise axis 130, to allow a surgeon to grip dilator 126 with surfaces of extensions 129 and turn dilator 126 around axis 130. While these engaging surfaces are shown as fins, any other extension or non-circular cross section of dilator 126 (when viewed along axis 130) can be useful to allow a surgeon or other user to twist dilator 126 into engagement with a tip of a needle (not shown) particularly for use in twisting a dilator to engage a threaded needle tip.

An implant as described can be implanted with the use of a surgical tool that includes an elongate needle portion ("needle") and a handle. The distal end or tip of the needle may be adapted to interconnect with the support member so the support member can be manipulated by the tool during installation of the support member. As described herein, the distal end of an end portion may include a tip such as a plastic tip (dilator) that connects to the end of the needle of a tool. The dilator can removably connect to the end of the needle in a fashion that resists removal during a surgical procedure, such as by snapping, using a threaded engagement, or otherwise removably engaging to the end of the tool (tip of the needle). A removable engagement is not a permanent engagement, but allows the tool to engage the dilator and be used to implant an end portion, then allows removal of the dilator from the tool, and then allows the tool to engage a second dilator on a second end portion of the same implant to allow the tool to be used to implant the second dilator through a second tissue path. The description of a dilator that can "removably" engage a tool does not include dilators that engage a tool and can be removed only by damage to the dilator, end portion, tool, or a sheath. As described, the "removable" engagement allows for a tool to be used during surgery to engage one dilator for insertion of the dilator through a tissue path, allows the tool to be removed from the dilator without substantial effort or damage to the implant or tool, and then allows the tool to engage a second dilator for implantation.

According to specific aspects of this description, a support member can be used to support vaginal vault tissue in a therapeutic position for treatment of vaginal vault prolapse, by attaching the tissue support portion of the support member to vaginal tissue and attaching an end portion or portions to separate locations to position or support the tissue. According to the invention, the end portion is passed through a tissue path that extends from the tissue support portion to an exterior incision exterior to a "coccyx region" of the patient. Specifically, the tissue path extends internally through tissue of a "coccyx region" bounded on one edge along the sacrospinous ligament (optionally either including or not including the sacrospinous ligament), another edge along the vertical side edge of the coccyx bone, another edge defined by a line from a tip of the coccyx bone to a point lateral to the tip by about 2.5 centimeters, and another edge that extends from that lateral point to the ischial spine.

Figure 11:
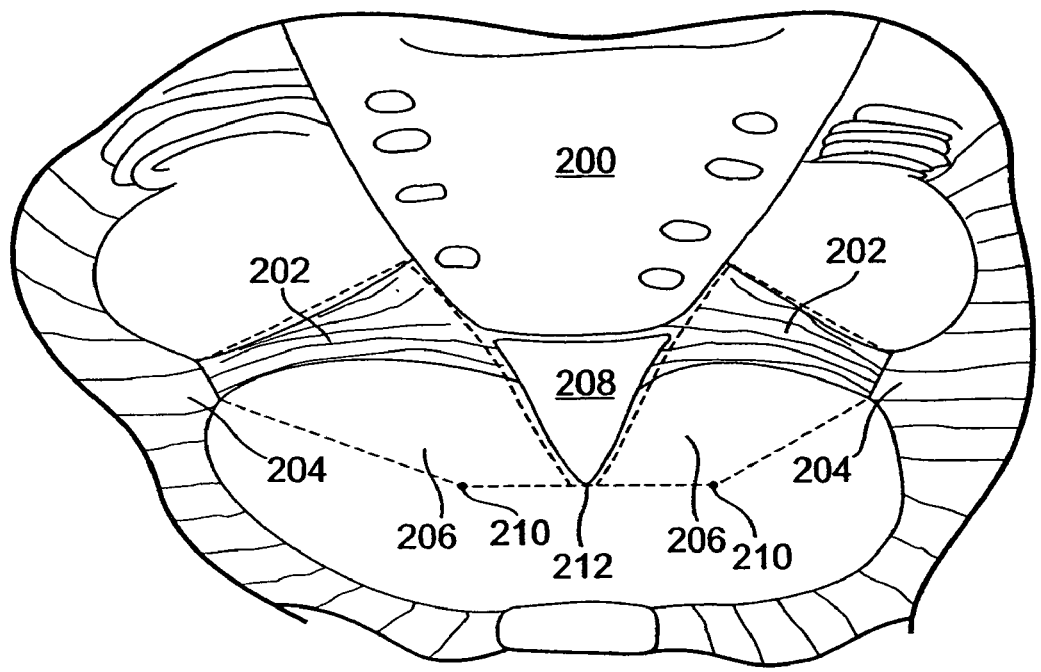
FIG. 11 illustrates pelvic anatomy with reference to a transcoccyx tissue path according to exemplary procedures of the invention.

One embodiment of a coccyx region 206 is shown at FIG. 11, which shows sacrum 200, sacrospinous ligaments 202 on each side of sacrum 200, and also connected to ischial spines 204. The lower tip 212 of coccyx bone 208 defines one corner of coccyx region 206 (in dashed lines). Ischial spine 204 defines another corner. The top edge of the connection of sacrospinous ligament 202 to sacrum 200 defines a third corner. Coccyx region 206 extends generally from the tip of the coccyx bone, along a side edge 209 of coccyx bone 208 and continuing along a lower side edge of sacrum 200 to the top edge of sacrospinous ligament 202, then across to ischial spine 204. The lower boundary, shown as the dashed line between ischial spine 204 and the tip 212 of coccyx 208, is not exactly straight between these points but goes from tip 212 through a point 210 that is approximately 2.5 centimeters lateral of tip 212, then further laterally and upward to ischial spine 204. The pudendal complex (not shown) travels laterally at a location that is above the upper edge of sacrospinous ligament 202, and is to be avoided.

Figure 12:
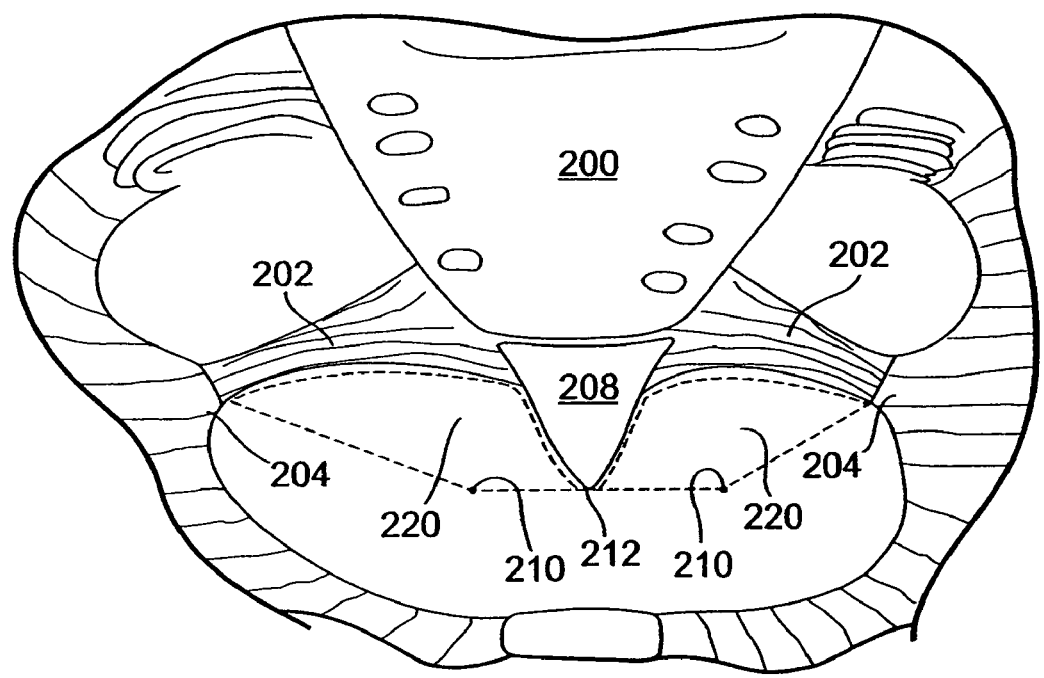
FIG. 12 illustrates pelvic anatomy with reference to a transcoccyx tissue path according to exemplary procedures of the invention.

A more specific coccyx region that can be a preferred coccyx region for a tissue path, is shown at FIG. 12, which shows anatomy similar to FIG. 11, but illustrates coccyx region 220 bounded by the lower edge of sacrospinous ligament 202, ischial spine 204, point 210 about 2.5 cm lateral to tip 212 of coccyx bone 208, and tip 212 of coccyx bone 208.

Figure 13:
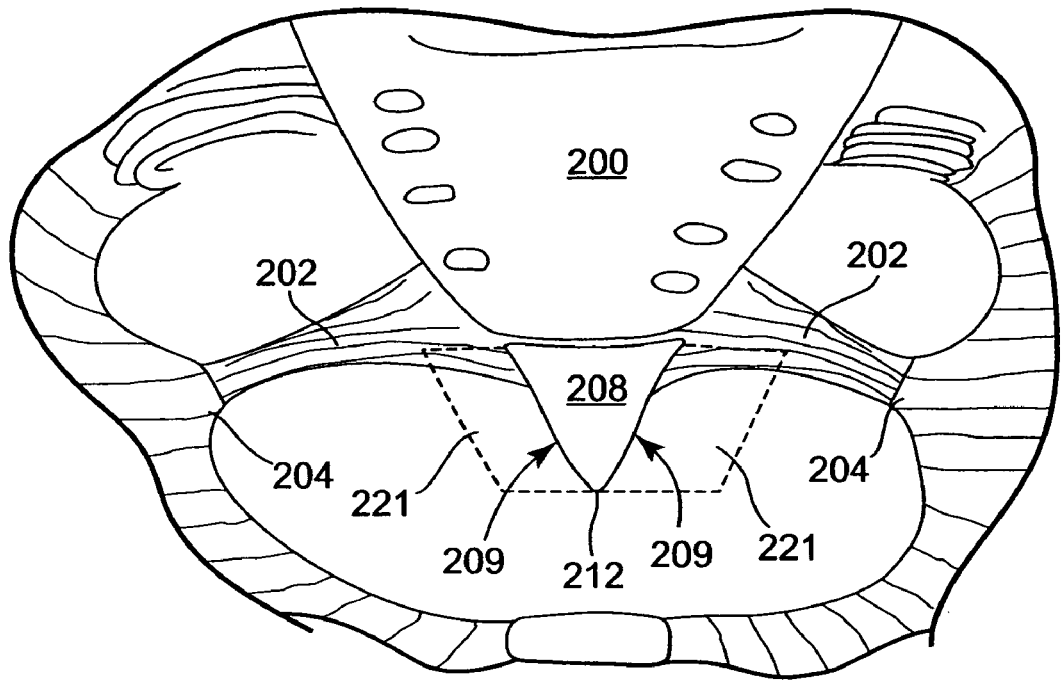
FIG. 13 illustrates pelvic anatomy with reference to a transcoccyx tissue path according to exemplary procedures of the invention.

Yet another embodiment of a preferred region for a tissue path is illustrated at FIG. 13 as region 221. Region 221 is generally the area lateral of either vertical edge of the coccyx bone, e.g., up to about 2.5 centimeters lateral of angled vertical edge 209 from bottom tip 212 of coccyx bone 208 to the top horizontal edge of the coccyx bone adjacent to the sacrum, e.g., a region bounded by a vertical edge of the coccyx bone between a tip of the coccyx bone at the bottom and a lower edge of a sacrum at the bottom, and a line 2.5 centimeters laterally from that edge of and parallel to the edge. As shown in FIG. 13, coccyx region 221 extends laterally a distance of up to 2.5 centimeters, including area lateral to the coccyx bone between an upper corner of coccyx bone 208 and tip 212.

As shown in FIG. 13, coccyx regions 221 may include a lower portion of sacrospinous ligament 202 lateral of each side of coccyx bone 208. According to different embodiments of region 221 and methods of the invention, a tissue path may be through this lower portion of sacrospinous ligament 202, or alternately a tissue path may be below this sacrospinous ligament, somewhere within region 221 and below the lower edge of sacrospinous ligament 202.

Exemplary methods and devices involve placement of a support member to support vaginal or other pelvic tissue with placement of an end portion at a location proximal to the coccyx bone. A tissue path as described herein, passing through a coccyx region, may be referred to herein as a "coccyx tissue path" or a "transcoccyx tissue path." Exemplary such tissue paths may extend through a coccyx region by also traversing ischiococcygeous muscle, iliococcygeous muscle, or possibly both, preferably avoiding gluteus maximus muscle.

Figure 14:
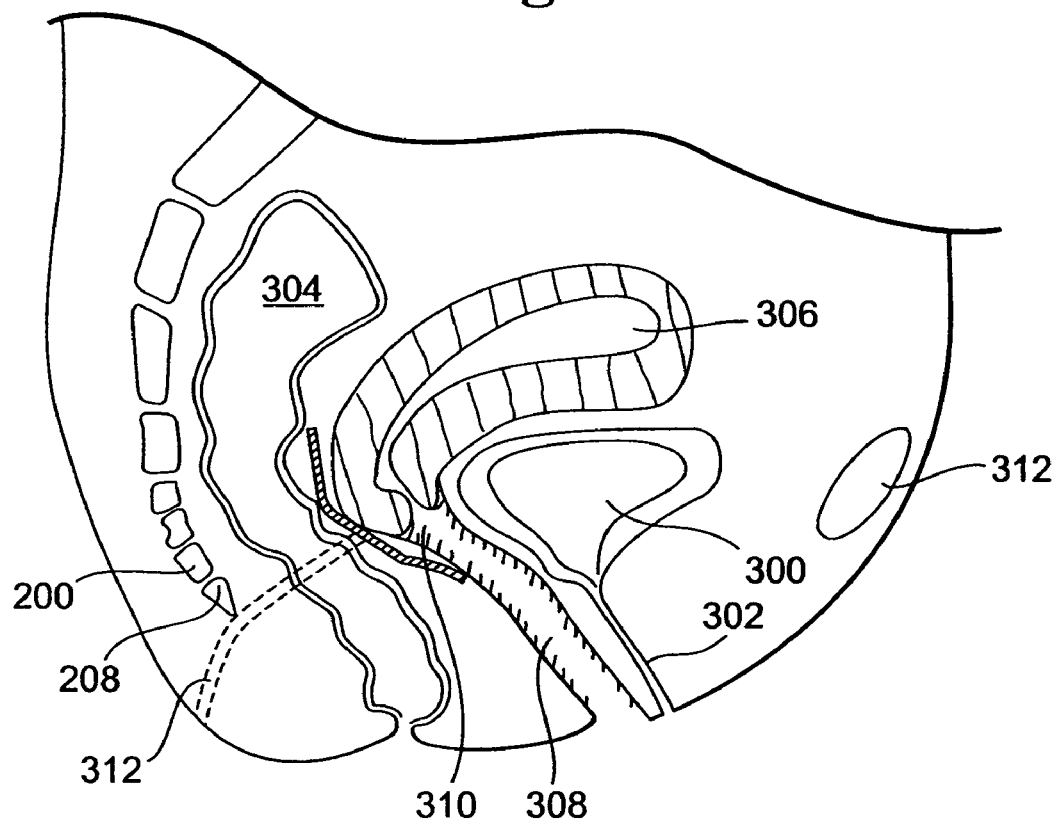
FIG. 14 illustrates pelvic anatomy with reference to a transcoccyx tissue path according to exemplary procedures of the invention.

FIG. 14 illustrates a side-view of an exemplary tissue path through a coccyx region, for passing an end portion through tissue starting at a region of vaginal vault tissue and extending past the rectum through a tissue path proximal to the coccyx bone. The end portion can generally be guided through such a passage prepared in muscle or other tissue, past the rectum, past and proximal to the coccyx bone, and then through an external incision (not shown). As illustrated in FIG. 14, relevant tissue and organs include bladder 300, urethra 302, sacrum 200, coccyx bone 208, rectum 304, and vagina 308. According to this exemplary embodiment of the invention, an implant includes tissue support portion 310 contacting pelvic tissue, as illustrated including the posterior vaginal and uterus. End portion 312 extends from tissue support portion 310, through a tissue path lateral of coccyx bone 208, and to an external incision in the buttocks region, the tissue path preferably not passing through gluteus maximum muscle.

Figure 15:
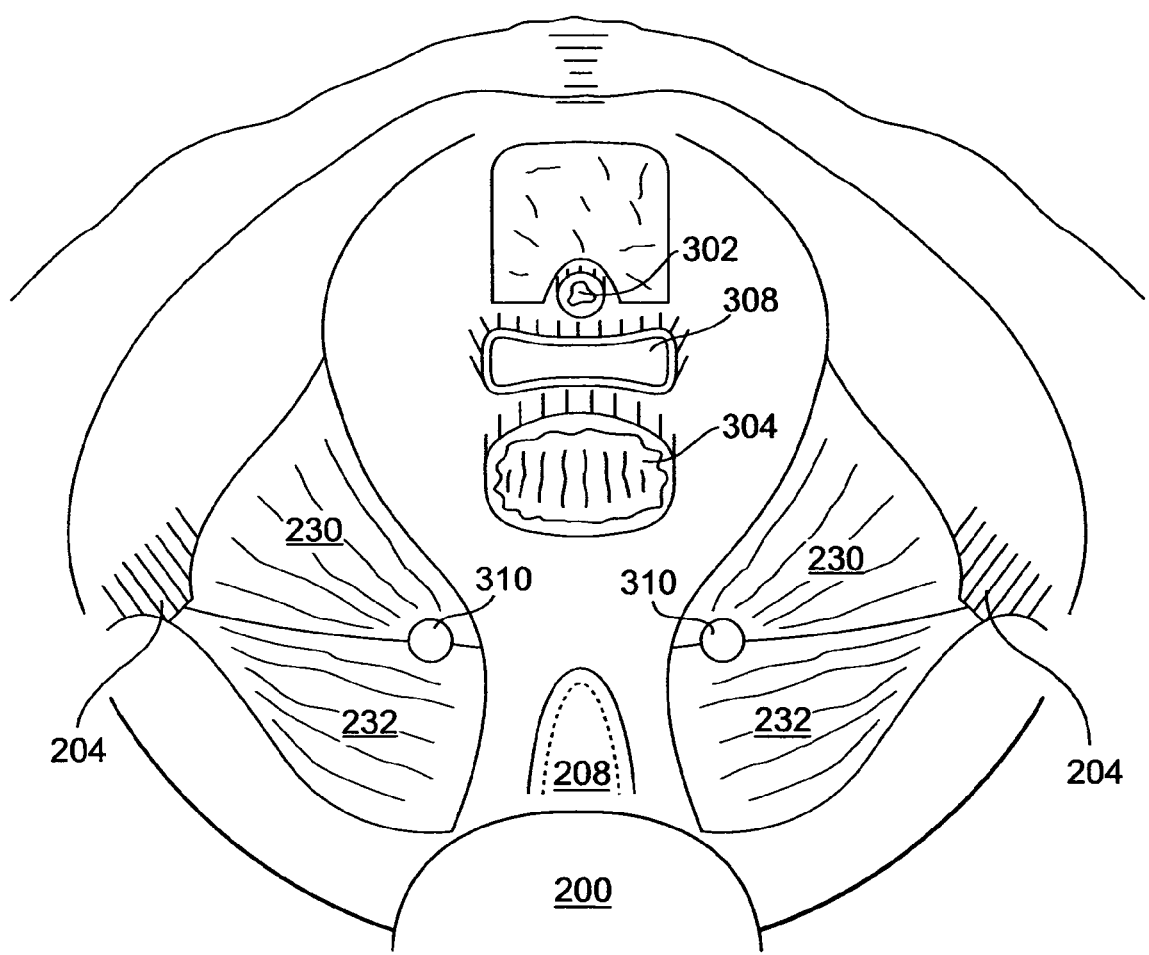
FIG. 15 illustrates pelvic anatomy with reference to a transcoccyx tissue path according to exemplary procedures of the invention.

FIG. 15 shows another view of a transcoccyx tissue path. As illustrated in FIG. 15, relevant tissue and organs include urethra 302, sacrum 200, coccyx bone 208, rectum 304, vagina 308, ischial spine 204, iliococcygeous muscle 230, and coccygeous muscle 232. An end portion of an implant (not shown) can be placed to extend through a tissue path that includes circles 310, and to an external incision.

Figure 16:
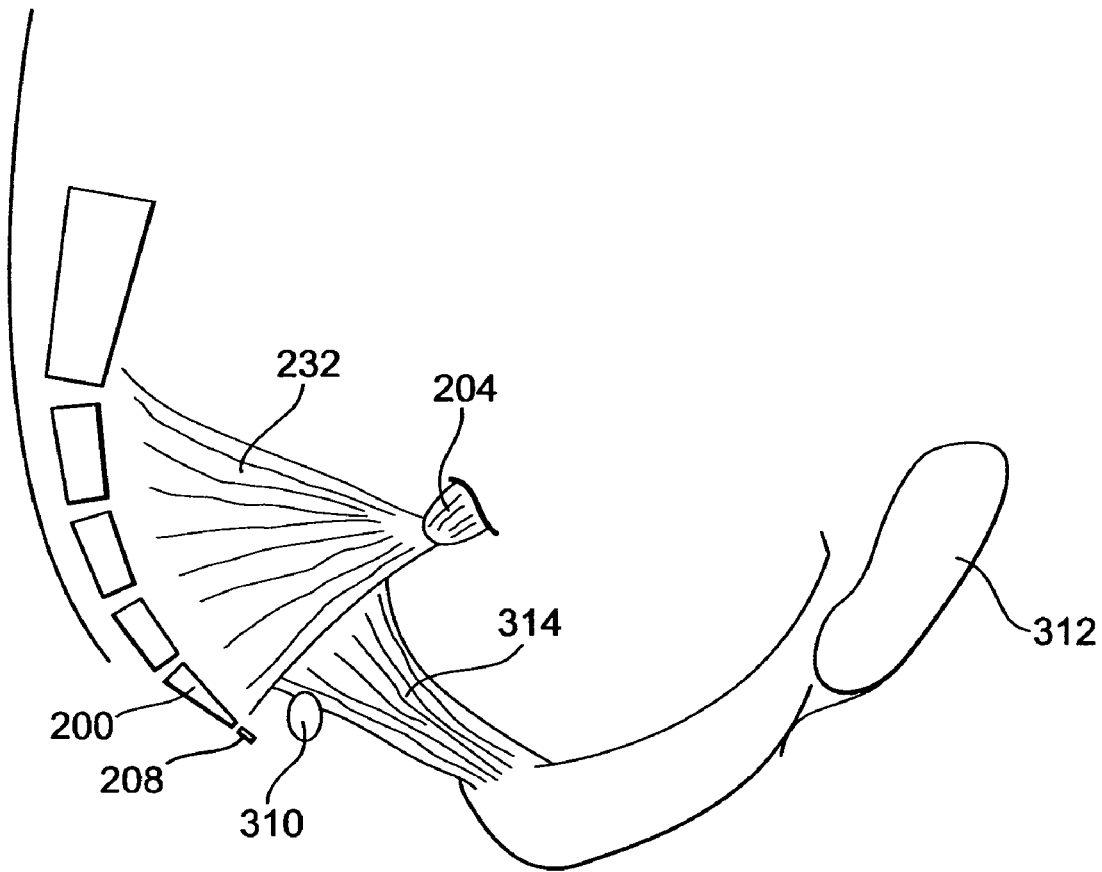
FIG. 16 illustrates pelvic anatomy with reference to a transcoccyx tissue path according to exemplary procedures of the invention.

Yet another side view of a transcoccyx tissue path is illustrated in FIG. 16, showing tissue and organs that include sacrum 200, coccyx bone 208, ischial spine 204, and coccygeous muscle 232. Also shown are pubic symphasis 312 and sacrotuberous ligament 314. According to this illustrated embodiment of the invention, an end portion (not shown) of an implant can be placed to extend through a tissue path that includes circle 310, and to an external incision, again preferably not passing through gluteus maximum muscle.

A tool can be used to install the support member, such as a tool described and illustrated in U.S. patent application Ser. No. 10/834,943. A useful tool generally includes a thin needle or trochar that attaches to a handle; a handle attached to an end of the trochar and that can optionally be removable; and a tip located at at least one end of the needle, optionally being sharp to be capable of producing a path when passed through tissue, optionally being adapted to removably attach to the handle, and optionally being adapted to firmly yet removably attach to an end portion of the support member. For example, a tip or "dilator" (e.g., of plastic) at an end of the end portion of the support member may removably attach to one or both ends of the needle or trochar, to allow the needle to push or pull the dilator through a tissue passage.

A particular needle for an "inside-out" (see, e.g., below) installation procedure for treating a female prolapse condition may include at least two curved portions, e.g., two curved portions of different radii of curvature and also optionally of different arclengths. A proximal end of a first curved portion can extend directly from a handle. The first curved portion is of a curvature and length that when inserted into the vagina can extend from the handle (located outside of the vagina) to the posterior vagina, e.g., the vaginal vault, or somewhat farther to the posterior. The first curved portion may mimic or approximate the shape and size of the vagina, allowing the needle portion distal from the first curved portion to be located at or posterior to the vaginal apex or vaginal vault during insertion and use. An exemplary length (arclength) of a first curved portion can be from 5 to 7 inches, e.g., from 5.5 to 6.5 inches. The radius of curvature of a first curved portion can be e.g., from 3 to 7 inches, e.g., from 3.5 to 6 inches. The radius of curvature may be substantially constant over the arclength, but may also vary by some degree.

Extending from a distal end of the first curved portion is a second curved portion of shorter length and a smaller radius of curvature. The second curved portion can be of a length and curvature to place a distal end of the second curved portion, or an extension thereof, in position to extend from the posterior vagina to an external incision, through a coccyx region as discussed herein (and preferably not through gluteus maximum muscle). The second curved portion includes a somewhat sharp corner, which is for both safety and for utility. For utility, a sharp turn causes the tip of the needle to be located near a coccyx region for creating a transcoccyx tissue path as described. The shortened length and radius also improve safety because the sharper turn prevents the tip from inadvertently contacting sensitive tissue located above the sacrospinous ligament (and between the Alcocks's canal and the sacrum) such as nerves and vessels of the pudendal complex. An exemplary length (arclength) of a second curved portion can be from 1 to 4 inches, e.g., from 1.5 to 3 inches. The radius of curvature of a second curved portion can be e.g., from 0.7 to 2 inches, e.g., from 1 to 1.5 inches. The radius of curvature may be substantially constant over the arclength of the second curved portion, but may also vary by some degree.

Extending from a distal end of the second curved portion is an optional extension portion. The extension may be curved or straight, and is of a length and curvature to place a distal end or tip of the needle in position to be located at an external incision, when the needle extends transvaginally through the vagina, through an incision in the posterior vagina, and through a coccyx region as discussed herein. A straight extension may be beneficial for producing a straight tissue path in that a straight needle portion may reduce trauma. Also, a straight needle portion may assist in puncturing tissue, such as stronger types of tissues, due to greater strength of a straight extension portion compared to a curved extension portion. If a needle tip includes a surface for engaging a dilator of an end portion, a straight portion at a needle tip may be useful compared to a curved tip, especially if the surface includes threads. The length of the extension is again based on utility and safety, with the length being selected to place the tip at a desired tissue location to create a transcoccyx tissue path and to avoid contacting sensitive tissue such as tissue of the pudendal complex that lies above the sacrospinous ligament. An exemplary length of this needle extension portion can be from 1 to 2 inches long, including an optional tip with a surface for engaging a dilator, such as threads.

A tool may include any type, shape, or size of a handle. According to certain embodiments, a handle or a portion of the length of a handle may exhibit a non-circular form when viewed along the longitudinal axis of the handle. The non-circular cross-section can be, e.g., an oval, rectangle, rhombus, etc., having one dimension (e.g., maximum dimension), a "width," that is greater than the dimension perpendicular to that "width." A non-circular form will provide one or more surfaces on the handle for a surgeon to place pressure onto and to achieve a grip. For example a flat portion may be present for placement of a thumb near the connection to the needle. The non-circular cross-sectional form also defines a midplane that is a plane that includes the longitudinal axis of the handle and extends along the width or the widest dimension of the handle when viewed in cross section along the longitudinal axis. According to preferred tools, the handle midplane can be perpendicular to a two-dimensional plane defined by the curved needle. An exemplary handle may be grasped by either hand with a thumb being located in the plane of the needle and having a flat portion below the thumb, to allow the thumb to apply pressure to the handle at the flat portion.

A non-circular handle, e.g., a handle with a midplane that is perpendicular to a two-dimensional needle, can be useful in a transvaginal inside-out procedure as described, where a needle is located within the vagina and pelvic region of a patient and out of view. A non-circular handle allows the user to understand the position of the needle tip during this or another "blind" procedure based on the known orientation between the handle and the needle tip, here a two-dimensional needle. A handle that includes a midplane perpendicular to a two-dimensional needle can be used by a surgeon with knowledge that the needle tip is always located in the plane perpendicular to the handle midplane.

Figure 17:
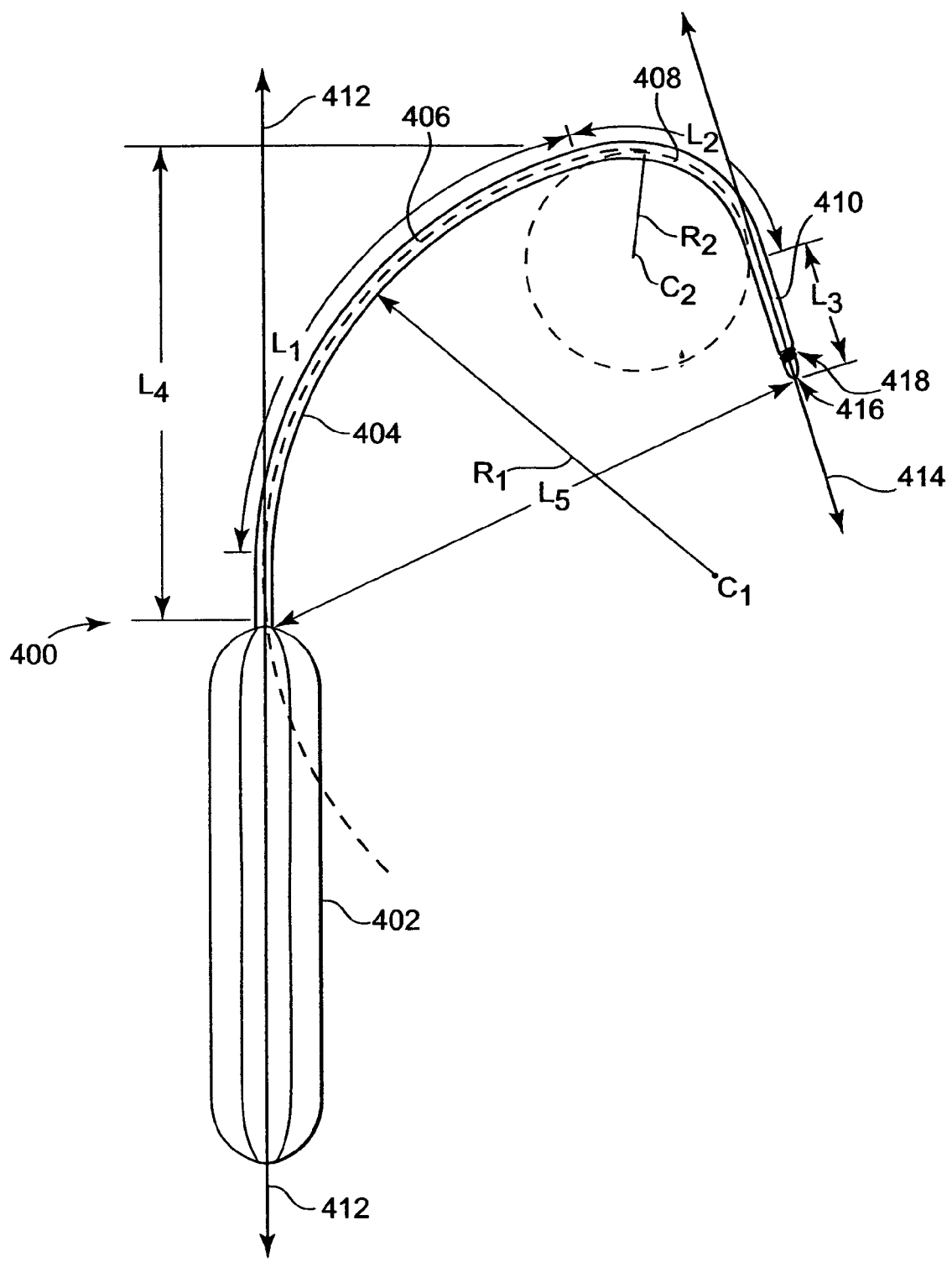
FIG. 17 illustrates an exemplary tool according to the invention.

FIG. 17 shows an exemplary tool for use in a transvaginal inside-out surgical implantation procedure, the needle including two curved portions, a straight extension, a handle having a midplane that is perpendicular to the two-dimensional plane of the needle, and a threaded tip. Tool 400 includes handle 402 having a midplane that is perpendicular to the plane of the page and to the plane defined by two-dimensional needle 404. Needle 404 includes a first curved portion 406 extending an arclength L1 and having a radius of curvature R1 based on center C1 of a circle defined by the curve of portion 406. The illustration shows portion 406 not being curved immediately from the connection to handle 402, but with a small amount of straight portion of needle between handle 402 and first curved portion 406; alternately, first curved portion 406 may begin immediately at the end of handle 402. Second curved portion 408 extends through an arclength L2 from a distal end of first curved portion 406. Portion 408 has a radius of curvature R2 based on center C2 of a circle defined by the curve of portion 408. The illustration shows second curved portion 408 beginning immediately at the distal end of first curved portion 406, but a small amount of straight portion of needle may be included between first curved portion 406 and second curved portion 408. Extending from a distal end of second curved portion 408 is straight portion 410 that terminates in tip 416, which includes threads (or another releasable engaging surface) 418. Threads 418 can be designed to engage an internal surface of a dilator, with the internal surface being either threaded or non-threaded. Handle 402 includes longitudinal axis 412, and line 414 is defined by extension 410 at tip 416. The angle between axis 412 and line 414 is approximately 10 degrees.

An exemplary length L3 of extension portion 410 can be from 1 to 2 inches long, including an optional tip with a surface for engaging a dilator, such as threads.

Still referring to FIG. 17, length L4 is the distance that is the greatest distance reached by needle 404 away from handle 402 as measured along axis 412. L4 can be any useful length that allows this exemplary tool to be used in an inside-out transvaginal procedure, such as a transcoccyx procedure. Examples of lengths for L4 may be from 4 to 6 inches, or from 4.5 to 5.5 inches.

Length L5 is the distance between the connection of needle 404 to handle 402, and tip 416, and can be any useful length that allows the tool to be used in an inside-out transvaginal procedure, such as a transcoccyx procedure. Examples of lengths for L5 may be from 4.5 to 6.5 inches, or from 5 to 6 inches.

The total length of a needle from connection to a handle to the end of the tip (including an engaging surface if any) may be as desired, e.g., from 9 to 11 inches, and the total angle traversed may be up to 180 degrees, meaning that the an axis of the needle through (or tangent to) the tip may point in a direction nearly parallel to the longitudinal axis of the handle. Exemplary angles between a line extending through or tangent to a tip of a needle (see line 414 of FIG. 17) and a longitudinal axis of a handle may be, e.g., 5 to 25 degrees, or from 10 to 20 degrees.

Exemplary methods of installing a support member according to the invention, e.g., use of a tool or implant described herein, can include certain steps described in U.S. patent application Ser. No. 10/834,943, with the understanding that certain exemplary methods and steps of the invention can include placement of an end portion of a support member of an implant at a tissue passage near the coccyx bone as described herein.

According to embodiments of a transvaginal surgical procedure, an incision can be made at the proximal posterior wall of the vagina, such as a midline incision at the apex of the vagina. Another incision can be made at the patient's exterior, i.e., an "external incision," which can at the epidermis such as external to the coccyx region at a position that can allow access to a transcoccyx tissue path as discussed. Exemplary tissue paths can be made starting at the incision at the vagina, passing through tissue proximal to the coccyx (i.e., through a coccyx region), past the rectum, optionally through the coccygeous or iliococcygeus muscle, and to the external incision. The path can advantageously avoid the gluteus maximus muscle.

Creation of the tissue path may be performed by use of a tool and dilator combination as described, which can create the tissue path and pass an end portion in a single step, or may alternately be performed by use of a separate dissecting tool, such as a sharp trochar or needle. As an example, a sharp tool, trochar, needle, or a sharp "pushable" dilator attached at an end of a needle as described herein, can be used to atraumatically prepare at least a portion of a tissue path as described. The tissue path may be dissected in either direction, from the vaginal incision in the direction of the external incision, or from the external incision in the direction of the vaginal incision. The same tool can be used to guide a tip (e.g., dilator) at the end portion of a support member through the tissue path and the external incision. An end portion of an implant may be led from an internal position such as at the region of the vaginal incision, through the tissue path, and to the external incision, by any method, and either by pushing or pulling the end portion through the tissue path. A support portion of the implant can be attached internally to tissue to be supported, at any time, before or after positioning one or more end portions through one or more tissue paths.

An exemplary method may be a transvaginal procedure that inserts the implant through an incision in the vagina and then pushes one or more end portions through one or more tissue paths starting internally and being dissected to an external incision in the region of the upper buttocks and the coccyx bone. This type of procedure, whereby an end portion is pushed from an internal position to an external incision, is referred to herein as an "inside-out" procedure.

Alternately, the procedure may insert the implant through an incision in the vagina. A surgical tool can be passed from an external incision, through a coccyx region, and to a vaginal region. An end portion of the implant is then associated with the tool, internally within the patient, and the tool is retracted to pull the end portion into position through the tissue path as the tool is withdrawn and removed. This type of procedure, whereby an end portion is pulled from an internal position to an external incision, is referred to herein as an "outside-in" type of procedure.

A particular example of an outside-in procedure may include an initial step of inserting an elongate tool such as a needle or trochar externally (at an external skin surface), through an external incision, and passing a tip of the tool through a coccyx region to a region at or near the vaginal apex. A vaginal incision is prepared at the posterior vagina for entry of an implant. The tip can be associated with an end portion of the implant at a position near the vaginal apex. The tool is retracted or removed by pulling the tool back through the tissue path, which pulls the end portion through the tissue path and through the external incision.

An example of an inside-out procedure may include a step of creating a vaginal incision at the posterior vagina for entry of an implant and a needle. A tip of a tool can be associated with an end portion of the implant, while both are located exterior to the patient. In particular, a dilator attached to the end portion of the implant can be removably engaged with a tip of an elongate insertion tool, e.g., a threaded needle tip. Optionally, as discussed herein, the tool can be a needle and the needle can be inserted into a sheath that surrounds the end portion, either through a side aperture in the sheath or an end opening, or by puncturing the sheath with the needle tip. The needle tip (or other tool associated with the end portion) and end portion are then inserted into the vagina and passed transvaginally through the vaginal incision. The dilator is pushed using the needle handle so the dilator creates a tissue path that includes a coccyx region as described herein, then to an external surface or an external incision on the surface of the coccyx region.

A particular inside-out method can involve the use of an implant that includes two end portions, one end portion having a length that is longer than the length of the other end portion. Each end portion is optionally included in a sheath as described herein, with the sheath of the longer end portion having a longer length. Implanting this "asymmetric" implant can include associating a needle (e.g., a needle with two different curved portions, as also described herein) with the shorter end portion, e.g., by inserting the needle into an end opening of the sheath or a side aperture of the sheath, and leading the needle through the inside length of the sheath to the dilator, then engaging the needle tip (optionally threaded) with the dilator. The needle and associated shorter end portion are inserted into the vagina and then transvaginally through a vaginal incision in the posterior vagina, then can be used to create a tissue path, e.g., that traverses a coccyx region as described herein, leading to an external incision. The dilator, extending from the external incision, e.g., near the coccyx region, is then disengaged from the needle tip and the needle is withdrawn from the sheath, tissue path, and vagina, leaving the sheath and end portion within the tissue path. The shorter end portion is positioned as desired within the tissue path and a support portion of the implant is located and positioned as desired at tissue to be supported, such as at the vaginal apex, or at other vaginal tissue, depending on the type of condition being treated. The amount of sheath and end portion that extend from the external incision are cut and the external incision may be closed, optionally with a suture to secure the distal end of the end portion to subcutaneous tissue. At least a portion of the longer end portion remains external to the patient extending from the vaginal opening. The longer end portion remains external to the vagina, and includes a sheath and end portion that are longer than those of the shorter end portion. The added length gives the surgeon additional material to work with after the first end portion has been installed and optionally positioned as desired and secured. The longer sheath may optionally include a side aperture through which the needle may be inserted, the aperture being a distance from the dilator that is approximately equal to the length of the sheath of the shorter end portion (i.e., the length between an end opening and a dilator of the shorter end portion). Equal distances allow the needle to be inserted the same distance within each sheath, while engaging the dilator. (Optionally, if the sheath does not include a side aperture, the needle top may be used to puncture the sheath at any desired position, to insert the needle to the inside of the sheath.) The second end portion is then installed through a tissue path on the opposite side of the first tissue path, e.g., in a coccyx region, leading to an external incision. The needle is disengaged and removed and the second end portion can be adjusted and positioned and secured as desired.

A "one-legged" implant, such as is shown at FIG. 2, can be implanted according to similar steps, as can implants that include more than two end portions.

Certain aspects of the methods and devices described herein relate to tools, implants, and methods for use in installing a pelvic implant as described, e.g., using one or a combination of: specific implants such as those having various types of sheaths (with openings or side apertures as described), end portions of different lengths, dilators of various designs and configurations, or support portion configurations; a transcoccyx tissue path; or a tool having two curved portions. In general, the described tools and implants may be used for treating various pelvic conditions such as urinary incontinence and prolapse, optionally but not necessarily using a transcoccyx tissue path. Certain of the described tools and implants may be particularly useful for treating one or the other of these conditions, e.g., certain tools or implants may be particularly useful for transvaginal installation of a support member for treating vaginal vault prolapse. Various other optional features of tools or implants include the following, may also be useful in combination with any of the tools, implant, or methods described.

A tool may optionally include a removable handle, i.e., a handle that is attachable and removable from an end of an elongate portion of a tool such as a needle or trochar. A tool that includes a removable handle can allow a needle or trochar to be completely passed through tissue without requiring a hole big enough to accommodate the handle. For example, certain methods of the invention can use a tool with the handle attached to initially place the pointed tip of a needle at a desired location through a vaginal incision, and then the pointed tip of the tool can be pushed through tissue and epidermis at a desired exit point to partially or completely establish a tissue path for an end portion of a support member. The handle of the tool can then be removed. An end portion of a support member (e.g., having a plastic tip such as a removable or locking dilator adapted to connect with and removable engage or lock to the tool at the end from which the handle was removed) can be connected to the end of the tool from which the handle was removed. The tool can then be pulled through the tissue passage to pull the end portion of the support member through the tissue passage.

Alternately or in addition, a tool may include a needle that includes a connection feature at an end that also can be attached to and removed from an implant, e.g., a needle may include a connection feature for attaching to a dilator that may then be pushed or pulled through tissue using the needle. The connection feature allows the needle to removably engage a dilator, or alternately may allow the dilator to be permanently snapped to the end of the needle, among other permanent or non-permanent engagements.

According to a general, exemplary design, a support member may include a pushable dilator attached at an end of an end portion, the dilator including a sharp tip design. The pushable dilator can be designed to fit the leading edge of a needle and to be pushed by the needle through tissue to either follow or produce a path in the tissue. To produce a path in the tissue by pushing the dilator through the tissue, the pushable dilator can be sufficiently sharp and rigid to pass through tissue when pushed with sufficient force using the needle.

A dilator (whether or not sufficiently sharp and rigid to be "pushable") may be straight, or, according to certain specific embodiments of the invention, may be curved in a manner that will improve manipulation of the dilator during a surgical procedure, e.g., in a manner that will facilitate pushing the dilator through tissue to either produce or follow a particular path of tissue. According to even more specific embodiments of the use of a curved dilator, the curved dilator may be used with a curved needle. Optionally, the curved shape or radius of the curved dilator can approximate or match the curved shape or radius of the curved needle.

Further design features can relate to dilators and needles that include anti-rotation or alignment features for use in various methods of treating pelvic conditions such as prolapse and urinary incontinence, in particular with the use of a curved needle and a curved dilator. The anti-rotation or alignment feature may be in the form of opposing and coordinated structural features of the dilator and the needle that together can: interconnect the dilator and needle to produce a desired alignment; prevent relative movement of the two pieces such as to prevent rotation of the dilator relative to the tool; or both. The alignment feature causes the dilator to be placed on the needle in a specific alignment, which if the needle and dilator are both curved as discussed above, causes the curve of the needle to be aligned with the curve of the dilator. An example of an alignment and anti-rotation feature is a keyed structure, as will be understood, that includes one or more inter-connecting surfaces and structures between the dilator and the needle to allow the dilator to connect to the needle when the two are properly aligned and then to also prevent rotation between the two when the two are connected. Other mechanical structures will also allow the dilator to be attached at an end of a needle in a manner to produce a desired alignment and to prevent rotation of the dilator relative to the needle.

These various features of tool and support member (e.g., dilator) designs can be useful, separately or in any combinations, when installing surgical articles or devices such as those of the pelvic region, including support members to treat urinary incontinence (male or female) and vaginal prolapse.

According to exemplary methods, tools and support members described herein can be useful for installing a support member to treat prolapse using a transvaginal method and a needle path originating inside of the body and continuing to an external location outside the body. A transvaginal approach, and features of tool and support member designs as described such as a pushable and curved dilator and a curved needle, can allow accuracy in attaching a support member to vaginal vault tissue, thereby improving speed and safety of the procedure.

According to certain other embodiments of methods and devices (optionally used in combination with other features described herein such as a curved needle, curved dilator, pushable dilator, sheath, etc.) a support member may include only a single end portion (e.g., at an apical region). Installation of such a support member (e.g., a "single-sided support" or "one-legged implant" as shown at FIGS. 2 and 3) can be faster and safer than installing a support member that includes two end portions for apical support. This can be particularly true when the end portion is to be passed through tissue of a coccyx region, because tissue at one side of the coccyx bone is easier to reach due to the sigmoid colon interfering with passage on the other side of the coccyx bone.

A dilator (e.g., a plastic tip) at an end of an end portion of a support member that is sufficiently rigid and pointed (e.g., sharp, conical, or the like) to be pushed through a tissue path, e.g., atraumatically to produce the path, allows for an alternate method of placing an end portion of a support member in a desired position. As an alternative to using a removable handle to pull an end portion of a support member through a tissue path that was previously established using a pointed needle, a "pushable" dilator may itself be pushed through tissue to establish a tissue path. For example, a rigid conical-shaped dilator could connect to an end of the needle, be inserted transvaginally to contact tissue, and be pushed through the tissue to create a transcoccyx or other tissue path. This will establish the tissue path while simultaneously passing the dilator and end portion through the tissue path, eliminating the need for a removable handle and the need for the needle to be pulled completely through a tissue pathway established first by the needle.

An optional curved dilator as described can advantageously produce reduced trauma through tissue when working around curves, because the curved dilator can reduce or eliminate the need for sweeping of the needle tip, and allow the operator to steer the tip by twisting the handle of the tool. A dilator that does not rotate relative to the needle (e.g., due to a keyed or similarly fixed connection between the needle and the dilator) can be particularly useful with a curved needle and a curved dilator. Preventing unwanted rotation of a curved dilator can, for example, allow for steering of the tip by twisting the handle.

The invention also relates to the use of combinations of tools and implants described herein, used together. As an example, the invention can involve a system, kit, or combination that includes any one of the described implants in combination with any one of the described tools. The system may be sterilized for commercial sale and ultimate use by surgeon. A kit or system may include, for a particular application or for treating a particular condition such as prolapse or incontinence: a support member (implant) and a tool designed for installing the support member, wherein the tool engages a dilator included as part of the support member. The tool and dilator features can be used for treating vaginal prolapse, and to install surgical implants or articles that are not related to the treatment of prolapse, such as for installing implants (e.g., slings) for the treatment of urinary incontinence.

Figure 18:
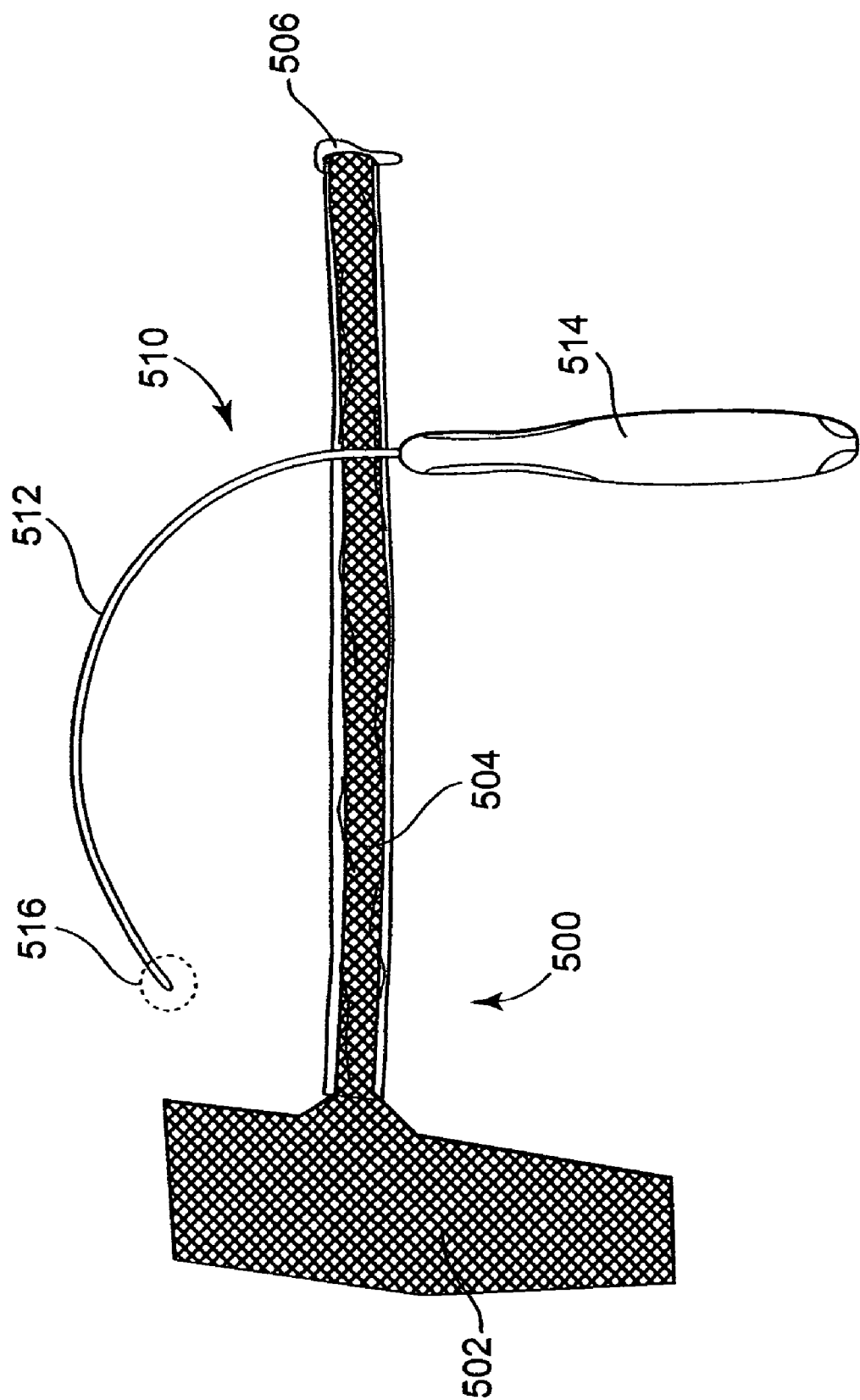
FIG. 18 illustrates an exemplary combination according to the invention.

FIG. 18 illustrates one example of a combination or kit that includes a tool 510 and a "one-legged" implant 500. Tool 510 includes a single curved portion 512 and tip 516 that is removably engagable with dilator 506 attached to a distal end of a mesh end portion 504 and a plastic sheath surrounding mesh end portion 504.

Figure 21:
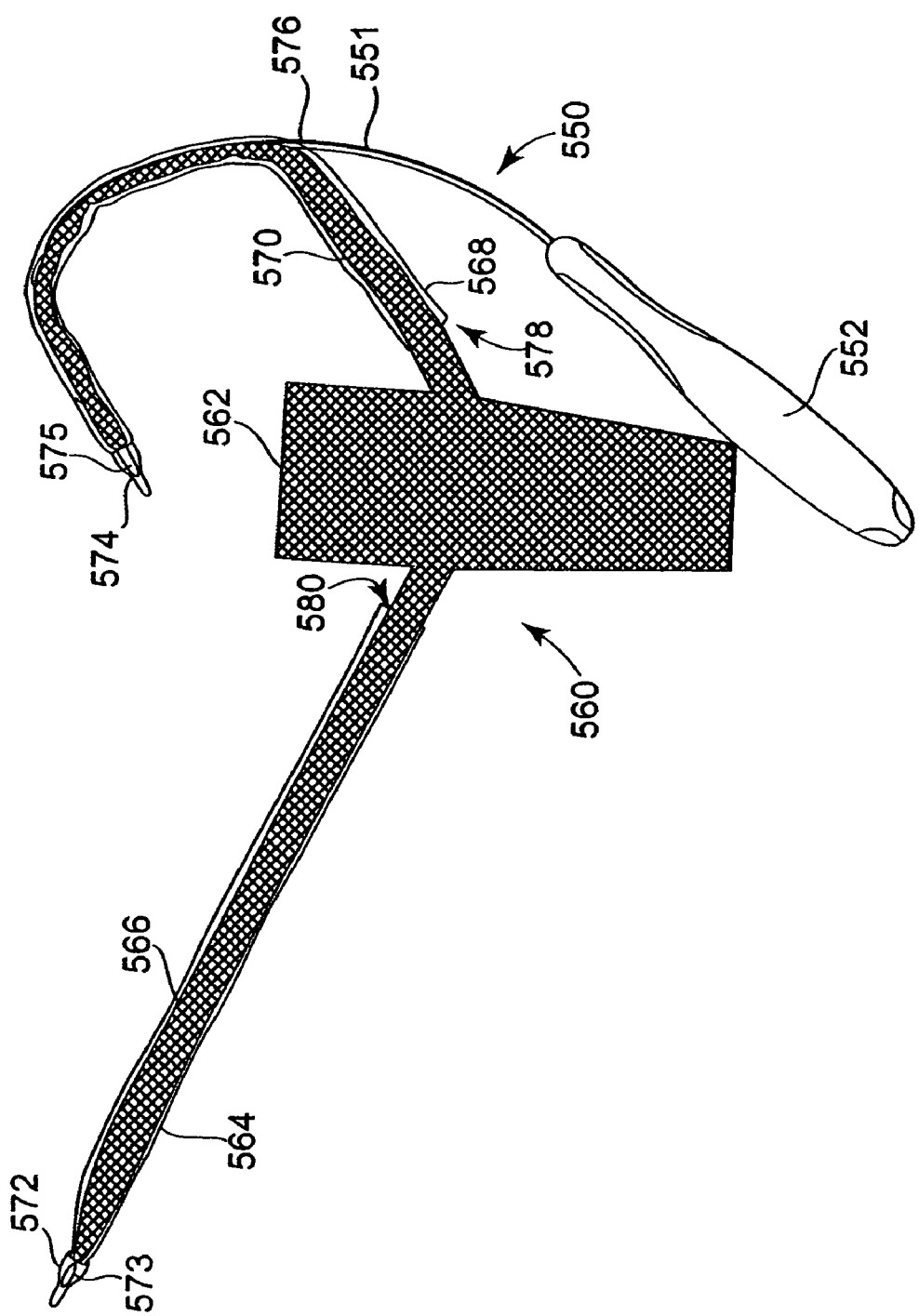
FIG. 21 illustrates an exemplary combination according to the invention.

FIG. 21 illustrates another example of a combination or kit, this one including tool 550 and implant 560. Tool 550 includes handle 552 and needle 551. Needle 551 is in two dimensions and as shown includes two curved portions, with a tip at the distal end. Handle 552 connects to a proximal portion of needle 551 and includes a midplane perpendicular to the plane defined by two-dimensional needle 551. Implant 560 comprises supportive portions consisting of mesh central support portion 562 located between mesh end portions 566 and 570, each end portion being located within a transparent plastic sheath 564 and 568, respectively. End portion 566 is a shorter end portion compared to longer end portion 570. Sheath 564 of shorter end portion 566 includes end opening 580 that allows a needle to enter sheath 566 and be extended within sheath 566 to engage internal surface 573 of dilator 572. Alternately, a needle may be used to puncture through sheath 564 at and location on sheath 564, to be led to and engage internal surface 573 of dilator 572. Sheath 568 of longer end portion 570 includes end opening 578, and also includes side aperture 576. Tool 550 is shown with needle 551 inserted through side aperture 576 into sheath 568 and extended within sheath 568 to dilator 574, where a tip 575 of needle 551 is inserted to engage an internal surface of dilator 574.

While FIG. 21 shows a single needle with a two-legged implant, the implant could alternately be configured, used, or sold, with two needles, optionally with each of the two needles being pre-inserted into a sheath with the tip of each needle engaged with the internal surface of the dilator at the end of each end portion.

Figure 22:
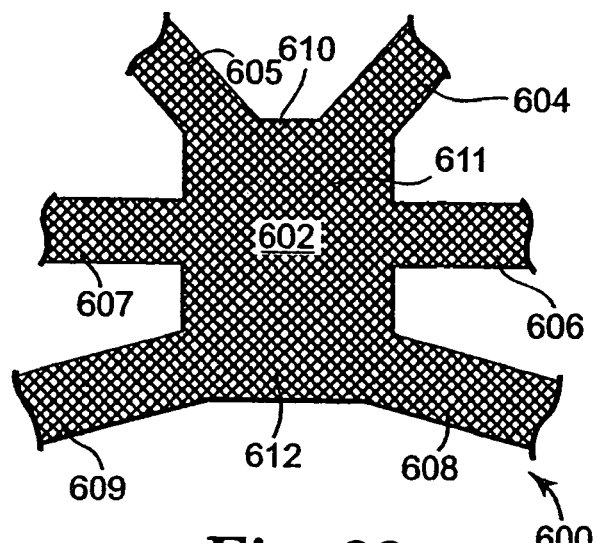
FIG. 22 illustrates an exemplary implant according to the invention.
Figure 23:
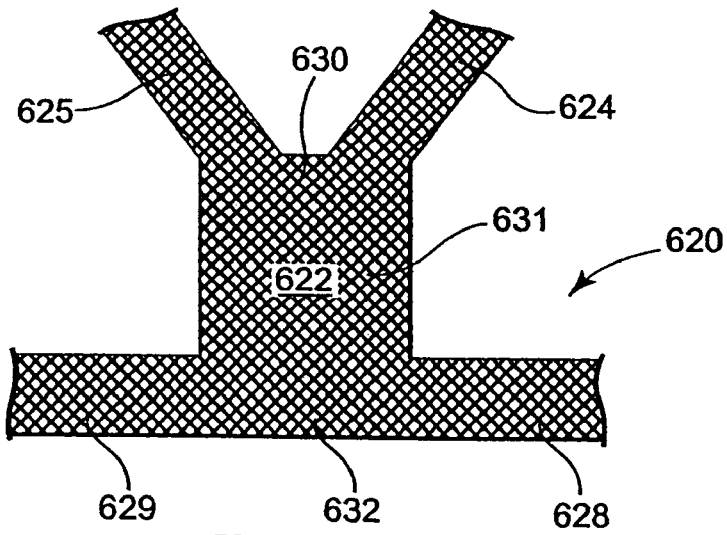
FIG. 23 illustrates an exemplary implant according to the invention.
Figure 24:
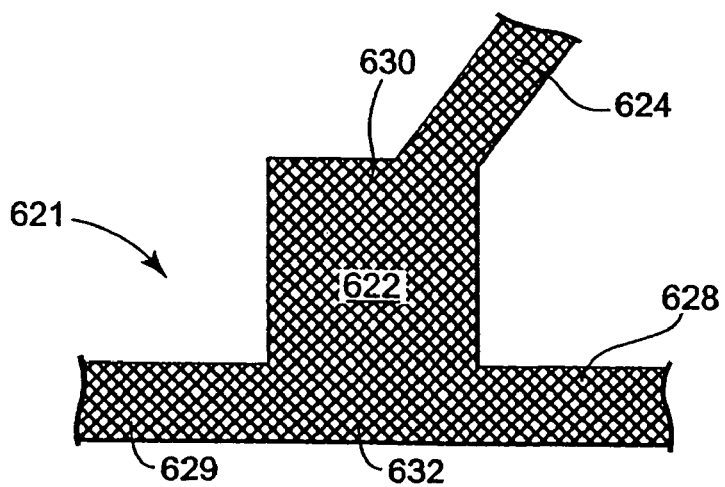
FIG. 24 illustrates an exemplary implant according to the invention.

FIGS. 22, 23, and 24, illustrate alternate embodiments of implants that can be useful with methods, tools, and end portion features (dilators, sheaths, different lengths) as described herein. The illustrated implants include a tissue support portion that can be used to contact anterior tissue of the vagina and related conditions. The implants are shown to include two end portions extending in generally or substantially opposite directions from the anterior portion, and optionally two end portions extending from a mid-portion of the tissue support portion. In addition, the implants include at least one end portion extending from the apical or posterior portion of the tissue support portion.

FIG. 22 illustrates mesh implant that includes tissue support portion 602, which includes posterior portion 610, mid-portion 611, and anterior portion 612, with end portions 604, 605, 606, 607, 608, and 609, attached to tissue support portion 602. Tissue support portion 602 can be implanted to contact vaginal tissue and nearby tissue, with posterior portion 610 being at an apical region and anterior portion 612 being anterior, e.g., placed beneath a bladder neck. End portions 606 and 607 can extend laterally, e.g., to a levator muscle. End portions 608 and 609 can extend laterally and to the anterior, such as to an obturator or through an obturator. End portions 604 and 605 can extend to the posterior, such as through a coccyx region, through a sacrospinous ligament, or through a coccyx region that includes a sacrospinous ligament. As illustrated, implant 600 includes two posterior end portions, 604 and 605, but another embodiment may only include one, e.g., 604, and may be installed using only a single tissue passage to the posterior, such as a single tissue passage through a coccyx region, through a sacrospinous ligament, or through a coccyx region that includes a sacrospinous ligament.

FIG. 23 illustrates mesh implant 620 that includes tissue support portion 622, which includes posterior portion 630, mid-portion 631, and anterior portion 632, with end portions 624, 625, 628, and 629, attached to tissue support portion 622. Tissue support portion 622 can be implanted to contact vaginal tissue and nearby tissue, with posterior portion 630 being at an apical region and anterior portion 632 being placed anteriorly, e.g., beneath a bladder neck. End portions 628 and 629 can extend laterally and to the anterior, such as to an obturator or through an obturator. End portions 624 and 625 can extend to the posterior, such as through a coccyx region, through a sacrospinous ligament, or through a coccyx region that includes a sacrospinous ligament. As illustrated, implant 620 includes two posterior end portions, 624 and 625, but another embodiment may only include one end portion, e.g., 624, and may be installed using only a single tissue passage to the posterior, such as a single tissue passage through a coccyx region, through a sacrospinous ligament, or through a coccyx region that includes a sacrospinous ligament. See FIG. 24, which illustrates implant 621, analogous to implant 620, but lacking a second posterior end extension and therefore including only one posterior end extension, 624.

Example of Procedure for "One-Legged" Implant

Figure 19:
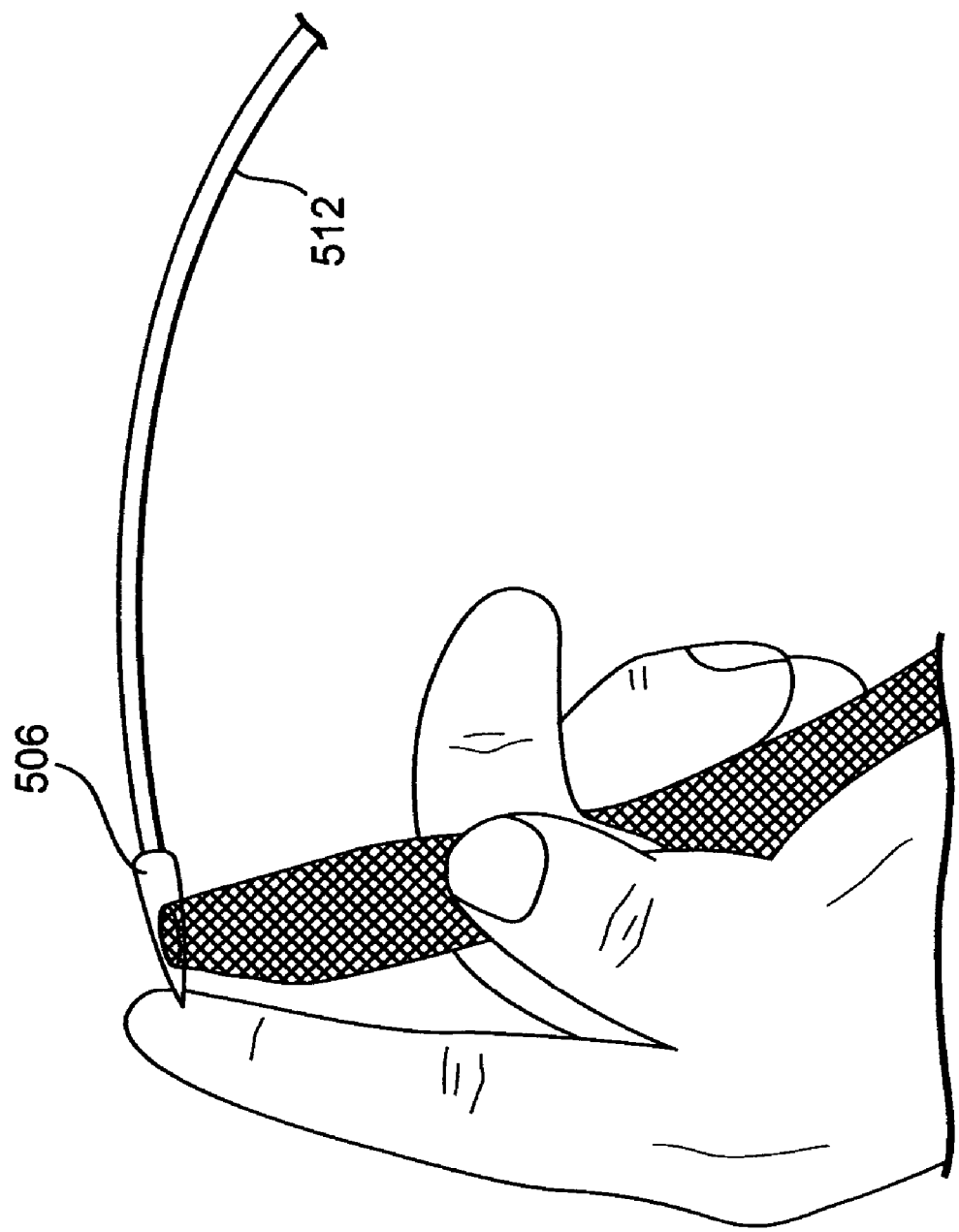
FIG. 19 illustrates a step of a method of the invention.
Figure 20:
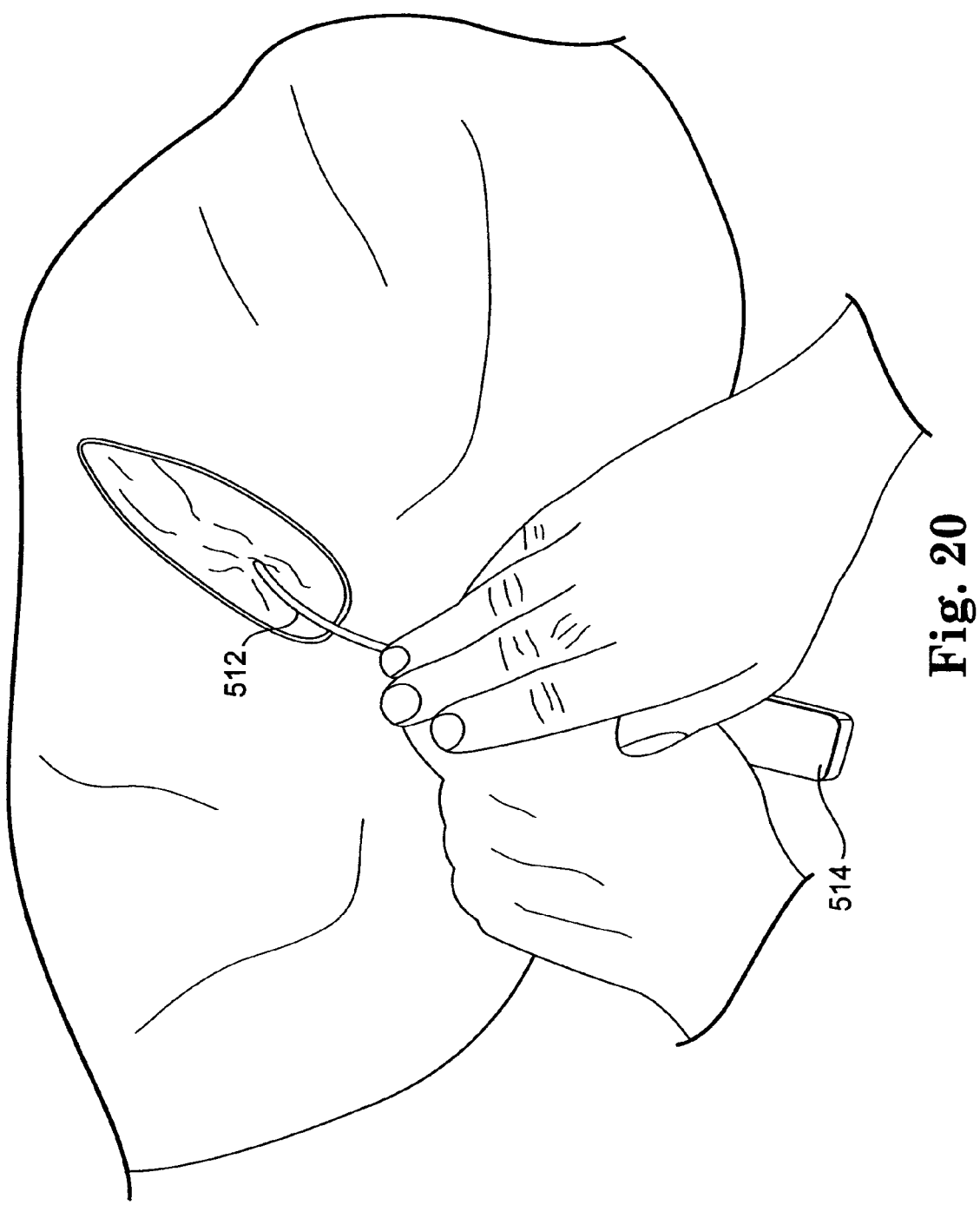
FIG. 20 illustrates a step of a method of the invention.

FIGS. 18 through 20 illustrate steps of a procedure for transvaginally installing a single-sided support member (i.e., a "one-legged" implant comprising a tissue support portion and only one end portion) to treat vaginal vault prolapse.

Generally, as shown at FIG. 18, the method involves providing a support member 500, which includes a tissue support portion 502 (for attachment to tissue of the vaginal vault) and a single mesh end portion 504 connected to the tissue support portion. End portion 504 is a mesh end portion that is contained in a plastic transparent sheath. At the distal end of the end portion 504 (the end not connected to tissue support portion 502), a plastic tip or "dilator" 506 is connected to mesh end portion 504 and its surrounding plastic sheath. Tool 510 is also provided, e.g., as part of a kit or system with support member 500. Tool 510 includes needle 512 and handle 514. Needle 512 is a single curve needle, but may alternately include two curved portions. Needle 512 includes tip 516, which engages pushable dilator 506 for passing through or creating a tissue path. Tip 516 of needle 512 can generally be designed to fit or otherwise engage dilator 506 in a configuration to allow needle 512 to push dilator 506 through tissue, transvaginally, during the procedure; for example tip 516 may be threaded to engage an internal surface of dilator 506 and allow needle 510 to push dilator 506. As illustrated, dilator 506 and then end of end portion 504 are not of a low profile configuration in that dilator 506 has a major dimension and is pushed in a direction that is perpendicular to the length-wise axis of end portion 504; in alternative embodiments, dilator 506 could be configured to be parallel with a length-wise axis of end portion 504, for easier passage through tissue of dilator 506 and the distal end portion.

An incision is provided at the posterior wall of the vagina.

A tissue path is prepared by initially dissecting the ischial spine, through the vaginal incision. The dilator is placed to engage the end of the needle (see FIG. 19). The needle is inserted into the external opening of the vagina and used to place the dilator, transvaginally, at a desired position for pushing the dilator through tissue.

FIG. 20 illustrates transvaginal placement of the dilator near the coccyx. In FIG. 20, the surgeon is holding handle 514, with a proximal portion of needle 512 being visible external to the vagina, and with the remaining needle and needle tip and implant being not visible but already placed internal to the patient through the vagina. The needle and dilator are used to puncture muscle layers approximately 1.5 to 2.5 centimeters lateral to the tip of the coccyx bone. The tissue path will run through iliococcygeous or coccygeous muscle but not the gluteus maximus. The path extends to the epidermis where an incision is made to allow the dilator to pass. The end portion can then be pulled through the tissue path externally and the tissue support portion of the support member can be positioned and attached to vaginal vault tissue.

Example of Insert-Molding Dilator to Distal End of End Portion and Sheath

In general, a low profile end configuration of a distal end of an end portion, such as shown at FIG. 7, can be prepared by any useful method, such as by insert molding a dilator to an assembly of an end portion contained within a sheath, the assembly being curled laterally.

Figure 8:
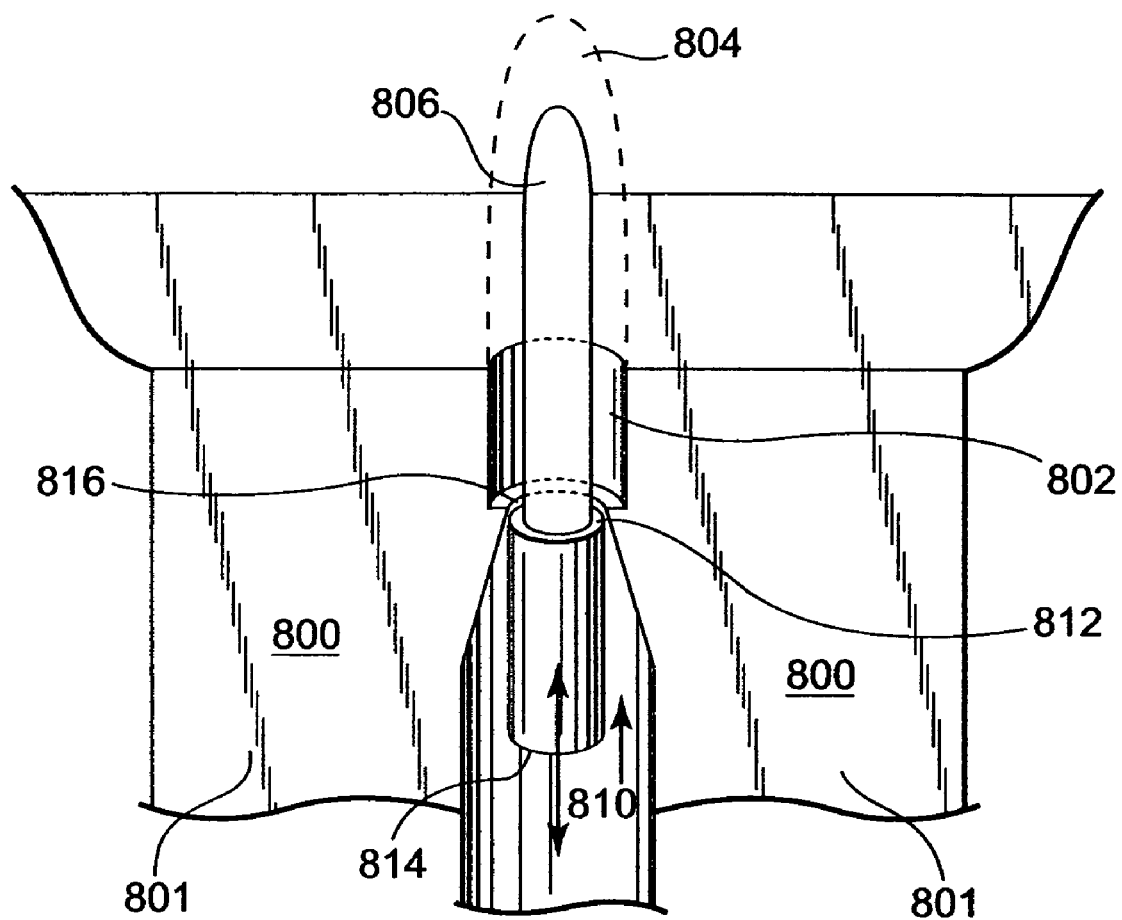
FIG. 8 illustrates a die useful for preparing a dilator described herein.

A useful mold can include a combination of a sheath-forming fixture and an insert mold. FIG. 8 illustrates a portion of a mold that includes a sheath-forming block 800 having side surfaces 801 that contact a second half (not shown) of the block 800. A dilator can be injection molded and formed within a cavity made up of lower mold cavity 802 and a connected upper mold cavity 804, shown in shadow (upper mold is not shown). Passage 816 is a circular passage defined by a lower end of cavity 802. Core pin 806 is inserted into passage 816 and works with cavities 802 and 804 to define an internal space of a dilator for engaging a tip of a needle. Core pin 806 includes integral collar 812 and shaft 814, and can be mounted in block 800 to be slidable between a position that allows end portion and sheath material to be threaded through passage 816, and a position at which collar 812 closes against a surface at the interior perimeter of block 800 that defines passage 816.

Figure 9:
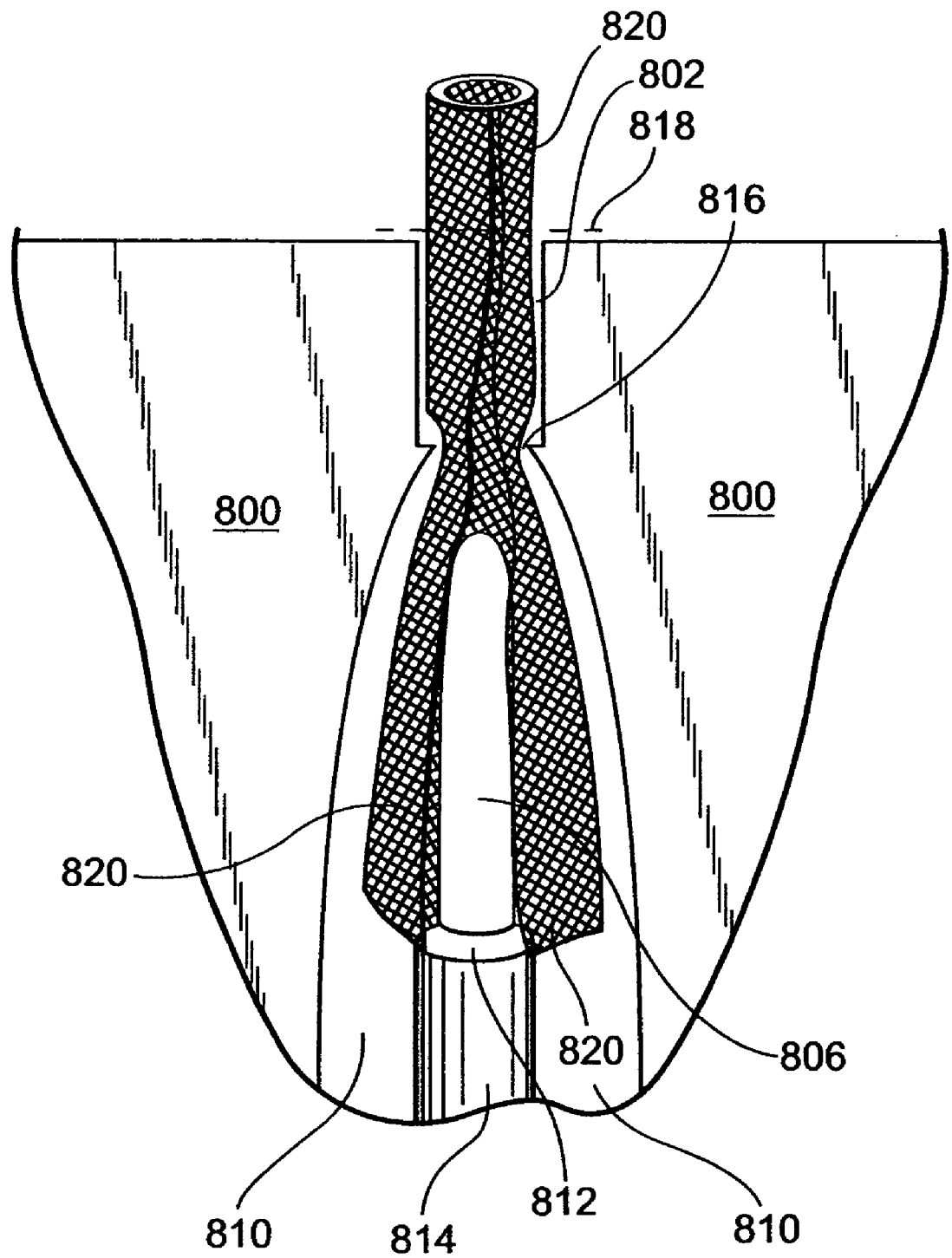
FIG. 9 illustrates a die useful for preparing a dilator described herein.

A mold such as shown in FIG. 8 can be used to produce a dilator connected to a distal end of an end portion and sheath. In general, as shown in FIG. 9, a sheath and end portion assembly 820 is threaded through guide channel 810 and passage 816 of block 800, into lower mold cavity 802, and can be cut at the top of cavity 802, e.g., at line 818. The end of the sheath is cut at an angle (not shown) and inserted into the bottom of the mold to thread through channel 810. As the sheath is pulled through the mold it rolls into a circular shape from the cone-shaped geometry in the mold at guide channel 810 below lower mold cavity 802. Excess sheath and end portion of assembly 820 can be cut off level with the top of the lower section of the mold, at line 818. Pin 806 is advanced up into the rolled sheath and mesh.

Figure 10:
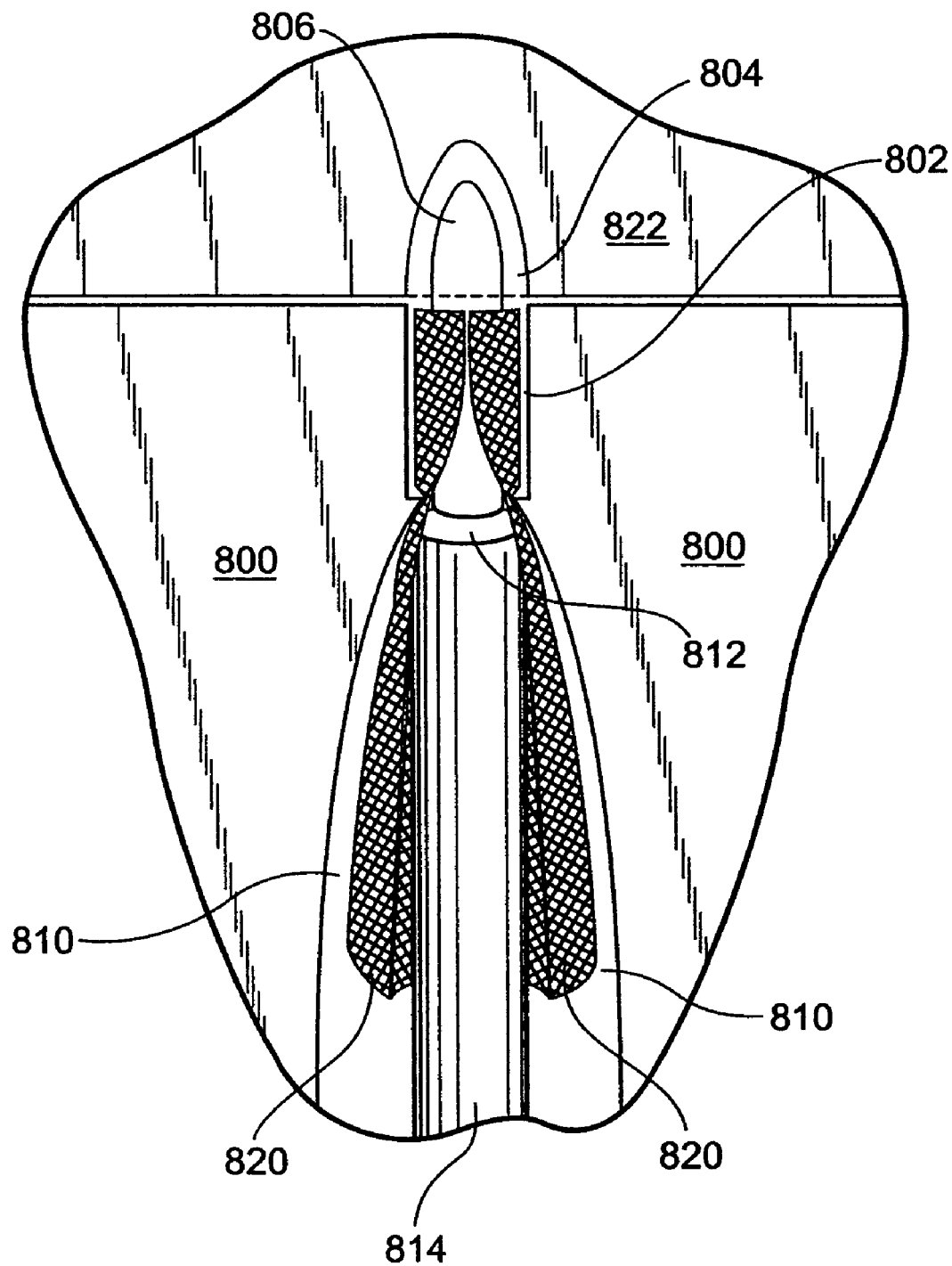
FIG. 10 illustrates a die useful for preparing a dilator described herein.

As shown in FIG. 10, pin 806 is moved up into lower cavity 802 and into upper mold cavity 804 of upper mold 822, placed in contact with the upper surface of block 800. Collar 812 seals against the bottom of lower mold cavity 802, with sheath and end portion assembly 820 being squeezed between collar 812 and block 800 at passage 816. The combined space of cavities 802 and 804 is then injected with a moldable dilator material such as a thermoplastic or thermosetting polymeric material using an injection press. The connector is formed and the sheath and end portion (mesh) assembly in the lower cavity of the mold is encapsulated making a single insert molded dilator that is connected to sheath and end portion assembly 820. The die is opened and a dilator, e.g., as shown in FIG. 7, has been attached.

The invention claimed is:

1. A method for supporting vaginal tissue, the method comprising:
   providing an implant comprising a tissue support portion and an end portion extending from the tissue support portion,
   creating a vaginal incision,
   placing the tissue support portion in contact with vaginal tissue in a position to support the vaginal tissue,
   producing a tissue path between the position of the tissue support portion and an exterior incision, the tissue path passing through tissue of a coccyx region bounded by an upper edge of a sacrospinous ligament, a tip of a coccyx bone, a point approximately 2.5 centimeters lateral to the tip of the coccyx bone, and an ischial spine,
   associating a tip of a needle with the end portion of the implant, and
   inserting the needle tip and associated end portion into the vagina and transvaginally through the vaginal incision, and
   pushing the needle tip and end portion of the implant through the tissue path and through the external incision thereby extending the end portion through the tissue path to the external incision.

2. The method of claim 1, wherein the method is for treatment of a condition selected from vaginal vault prolapse, enterocele, rectocele, cystocele, and combinations thereof.

3. The method of claim 1, wherein the tissue path passes through a coccyx region bounded by a lower edge of a sacrospinous ligament, a tip of a coccyx bone, a point approximately 2.5 centimeters lateral to the tip of the coccyx bone, and an ischial spine.

4. The method of claim 1, wherein the tissue path passes through a coccyx region bounded by an edge of the coccyx bone between a tip of the coccyx bone and a lower edge of a sacrum, and a line 2.5 centimeters from the edge of the coccyx bone lateral and parallel to the edge.

5. The method of claim 1, wherein the tissue path passes from a region of the vaginal apex, through coccygeous or iliococcygeous muscle, to the external incision.

6. The method of claim 1, wherein the tissue path does not traverse gluteus maximus muscle.

7. The method of claim 1, wherein the implant comprises supportive portions consisting of a tissue support portion and only one end portion, and the method includes making only one tissue path between the vaginal apex region and the external incision, for passing the one end portion between the vaginal apex region and the external incision.

8. A method of claim 1, further comprising using a surgical tool comprising
   a handle comprising a longitudinal axis,
   a two-dimensional elongate needle extending from the handle, the elongate needle comprising
      a first curved portion proximal to the handle, the first curved portion having a first radius of curvature and a first arclength,
      a second curved portion extending from a distal end of the first curved portion, the second curved portion having a second radius of curvature and a second arclength that are different from the first radius of curvature and first arclength, and
      and a straight portion extending from a distal end of the second curved portion to a needle tip.

9. The method of claim 1, wherein the implant comprises a dilator at an end of the end portion distal from the tissue support portion, the dilator capable of cooperating with the insertion tool to push or pull the dilator through tissue.

10. The method of claim 1, wherein the implant comprises an elongate sheath surrounding at least a portion of an end portion, and a dilator attached at a distal end of the sheath.

11. A method of treating a pelvic condition, the method comprising
   providing an implant comprising supportive portions consisting of
      a central support portion having two opposing sides and two opposing ends and
      a shorter end portion extending from one end of the central support portion and a longer end portion extending from the opposing end of the central support portion
      wherein the central support portion has a width greater than a width of the end portions, and
      the shorter end portion has a length that is shorter than a length of the longer end portion
   providing a tool comprising a curved needle, a tip of the needle adapted to engage a distal end of an end portion,
   contacting the tissue support portion with a pelvic tissue,
   engaging the tool with a distal end of the shorter end portion and implanting the shorter end portion in a patient, and
   after implanting the shorter end portion, engaging the tool with a distal end of the longer end portion and implanting the longer end portion in the patient.

12. The method of claim 11, for treating vaginal vault prolapse.

13. A method of implanting a pelvic implant, the method comprising
   providing an implant comprising:
      a tissue support portion and first and second elongate end portions extending from the tissue support portion,
      a first and second dilator attached to a distal end of each end portion,
      first and second elongate sheaths surrounding at least a portion of each end portion, the sheaths comprising a distal end attached to the dilator,
   wherein
      the end portions include a passage inside of the sheaths, to an internal surface of each dilator,
   providing a tool comprising an elongate needle having a needle tip adapted to engage the internal surface of the dilators through the passages,
   placing the tool inside at least a portion of the first sheath surrounding a length of the first end portion, and engaging the first dilator,
   inserting the first dilator through a first tissue path by pushing the first dilator using the tool.

14. The method of claim 13, further comprising:
   disengaging the first dilator from the needle tip,
   withdrawing the needle from the first tissue path,
   after withdrawing the needle from the first tissue path, inserting the needle into the sheath of the second end portion surrounding a length of the second end portion and engaging a second dilator with the needle tip, and
   inserting the second dilator through a second tissue path by pushing the second dilator using the tool.

15. A method for supporting vaginal tissue, the method comprising
   providing an implant comprising a tissue support portion and an end portion extending from the tissue support portion,
   creating a vaginal incision,
   placing the tissue support portion in contact with vaginal tissue in a position to support the vaginal tissue,
   producing a tissue path between the position of the tissue support portion and an exterior incision, the tissue path passing through tissue of a coccyx region bounded by an upper edge of a sacrospinous ligament, a tip of a coccyx bone, a point approximately 2.5 centimeters lateral to the tip of the coccyx bone, and an ischial spine,
   extending the end portion through the tissue path to the external incision,
wherein the implant comprises supportive portions consisting of a tissue support portion and only one end portion, and the method includes making only one tissue path between the vaginal apex region and the external incision, for passing the one end portion between the vaginal apex region and the external incision.

* * * * *